US009844607B2

(12) United States Patent
Kruip et al.

(10) Patent No.: US 9,844,607 B2
(45) Date of Patent: *Dec. 19, 2017

(54) IMMUNO IMAGING AGENT FOR USE WITH ANTIBODY-DRUG CONJUGATE THERAPY

(71) Applicants: SANOFI, Paris (FR); The Board of Trustees of the Leland Stanford Junior University, Palo Alto, CA (US)

(72) Inventors: Jochen Kruip, Erzhausen (DE); Sanjiv S. Gambhir, Portola Valley, CA (US); Susanta K. Sarkar, Cambridge, MA (US); Mathias Gebauer, Frankfurt (DE); Christian Lange, Frankfurt (DE); Ingo Focken, Hocheim (DE); Richard Kimura, Stanford, CA (US); Arutselvan Natarajan, Sunnyvale, CA (US); Ohad Ilovich, Sunnyvale, CA (US)

(73) Assignees: SANOFI, Paris (FR); THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 63 days.

This patent is subject to a terminal disclaimer.

(21) Appl. No.: 14/173,638

(22) Filed: Feb. 5, 2014

(65) Prior Publication Data

US 2014/0255305 A1    Sep. 11, 2014

Related U.S. Application Data

(60) Provisional application No. 61/761,188, filed on Feb. 5, 2013.

(51) Int. Cl.
*A61K 39/00* (2006.01)
*C07K 16/28* (2006.01)
*A61K 51/10* (2006.01)
*A61K 39/395* (2006.01)
*C07K 16/30* (2006.01)

(52) U.S. Cl.
CPC .... *A61K 51/1045* (2013.01); *A61K 39/39591* (2013.01); *C07K 16/3092* (2013.01); *C07K 2317/24* (2013.01); *C07K 2317/35* (2013.01); *C07K 2317/55* (2013.01); *C07K 2317/626* (2013.01); *C07K 2317/64* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 6,596,503 B1 | 7/2003 | Wennerberg et al. |
| 2004/0220388 A1 | 11/2004 | Mertens et al. |
| 2007/0041980 A1* | 2/2007 | Payne .............. A61K 47/48384 424/155.1 |
| 2008/0050311 A1* | 2/2008 | Goldenberg ..... A61K 47/48369 424/1.49 |
| 2009/0099336 A1 | 4/2009 | Payne et al. |
| 2010/0076178 A1* | 3/2010 | Ghayur ................. C07K 16/28 530/387.3 |
| 2010/0301855 A1* | 12/2010 | Hyde ................... G01R 33/383 324/309 |
| 2011/0212094 A1 | 9/2011 | Ghayur et al. |
| 2011/0280800 A1* | 11/2011 | Wu ....................... A61K 9/0019 424/1.49 |
| 2014/0256916 A1* | 9/2014 | Kruip ................. G01N 33/5308 530/387.3 |

FOREIGN PATENT DOCUMENTS

| WO | WO 02/02781 | 1/2002 |
| WO | 2005009369 | 6/2005 |
| WO | WO 2007/024222 | 3/2007 |
| WO | 2011036460 | 3/2011 |
| WO | WO 2011/028811 | 3/2011 |

OTHER PUBLICATIONS

Ferreira et al., Eur J Nucl Med Mol Imaging, 37:2117-2126, 2010.
Bornhorst et al., Methods Enzymol. 326:245-254, 2000.
Fritzberg et al., Proc. Natl. Acad. Sci. USA 85: 4025-4029, 1988.
Non-Final Office Action from U.S. Appl. No. 14/173,656, dated Nov. 23, 2015.
International Preliminary Report on Patentability from International Application No. PCT/US2014/014903, dated Aug. 11, 2015.
International Preliminary Report on Patentability from International Application No. PCT/IB2014/000279, dated Aug. 11, 2015.
Kearse et al. (2000). Monoclonal antibody DS6 detects a tumor-associated sialoglycotope expressed on human serous ovarian carcinomas. Int J Cancer, 88(6):866-72.
Liu et al. (2010). 18F-labeled galacto and PEGylated RGD dimers for PET imaging of avβ3 integrin expression. Mol Imaging Biol., 12(5): 530-8.
Williams et al. (2008). Review: update on selection of optimal radiopharmaceuticals for clinical trials. Cancer Biother Radiopharm., 23(6):797-806.
Carrigan et al. (2008). 525 Poster Preclinical evaluation of SAR566658 (huDS6-DM4) in mice bearing human tumor xenografts of breast, ovarian, lung, cervical and pancreatic cancer. European Journal of Cancer Supplements, 6(12): 166.
Hughes et al. (2000). Targeting superficial bladder cancer by the intravesical administration of copper-67-labeled anti-MUC1 mucin monoclonal antibody C595. J. Clin. Oncol., 18(2): 363-70.
Ionescu et al. (2008). Contribution of variable domains to the stability of humanized IgG1 monoclonal antibodies. Journal of pharmaceutical sciences, 97(4): 1414-1426.
International Search Report from International Application No. PCT/US2014/014903, dated Apr. 4, 2014.

(Continued)

*Primary Examiner* — Julie Wu
(74) *Attorney, Agent, or Firm* — McDonnell Boehnen Hulbert & Berghoff LLP

(57) ABSTRACT

The invention relates to a companion diagnostic antibody-like binding protein based on the humanized monoclonal antibody, DS6, to be used as diagnostic tool for in vivo detection and quantification of the tumor-associated MUC1-sialoglycotope, CA6.

12 Claims, 14 Drawing Sheets

(56) References Cited

OTHER PUBLICATIONS

International Search Report from International Application No. PCT/IB2014/000279, dated Jun. 25, 2014.
Lewis et al. (2003). In vivo evaluation of pretargeted 64Cu for tumor imaging and therapy. Journal of Nuclear Medicine, 44(8): 1284-92.
Medarova et al. (2009). Multiparametric monitoring of tumor response to chemotherapy by noninvasive imaging. Cancer Res., 69(3): 1182-89.
Natarajan et al. (2008). Development of multivalent radioimmunonanoparticles for cancer imaging and therapy. Cancer Biother. Radiopharmaceuticals, 23(1): 82-91.
Salouti et al. (2011). Preparation and biological evaluation of Lu-177 conjugated PR81 for radioimmunotherapy of breast cancer. Nuclear Medicine and Biology, 38(6): 849-855.
Tampellini et al. (2006). Prognostic significance of changes in CA 15-3 serum levels during chemotherapy in metastatic breast cancer patients. Breast Cancer Res Treat 98(3): 241-8.
Written Opinion of the International Searching Authority from International Application No. PCT/US2014/014903, dated Apr. 4, 2014.
Written Opinion of the International Searching Authority from International Application No. PCT/IB2014/000279, dated Jun. 25, 2014.
Ilovich et al., "Development and Validation of an Immuno-PET Tracer as a Companion Diagnostic Agent for Antibody-Drug Conjugate Therapy to Target the CA6 Epitope," Radiology 276(1):191-8 (Jul. 2015).
Ofran et al., "Automated Identification of Complementarity Determining Regions (CDRs) Reveals Peculiar characteristics of CDRs and B Cell Epitopes," J. Immunol. 181(9):6230-5 (Nov. 2008).
Non-Final Office Action for U.S. Appl. No. 14/173,656, dated Apr. 25, 2017 (pp. 1-7).
Final Office Action for U.S. Appl. No. 14/173,656, dated Jun. 27, 2016 (pp. 1-23).

* cited by examiner

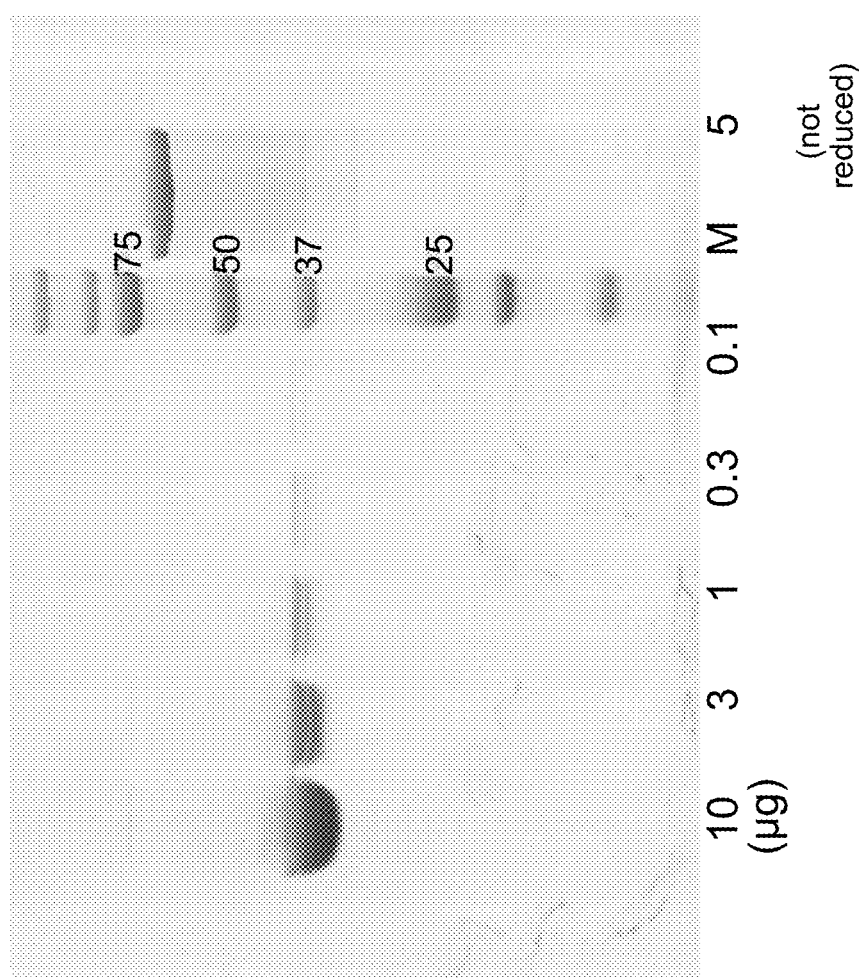

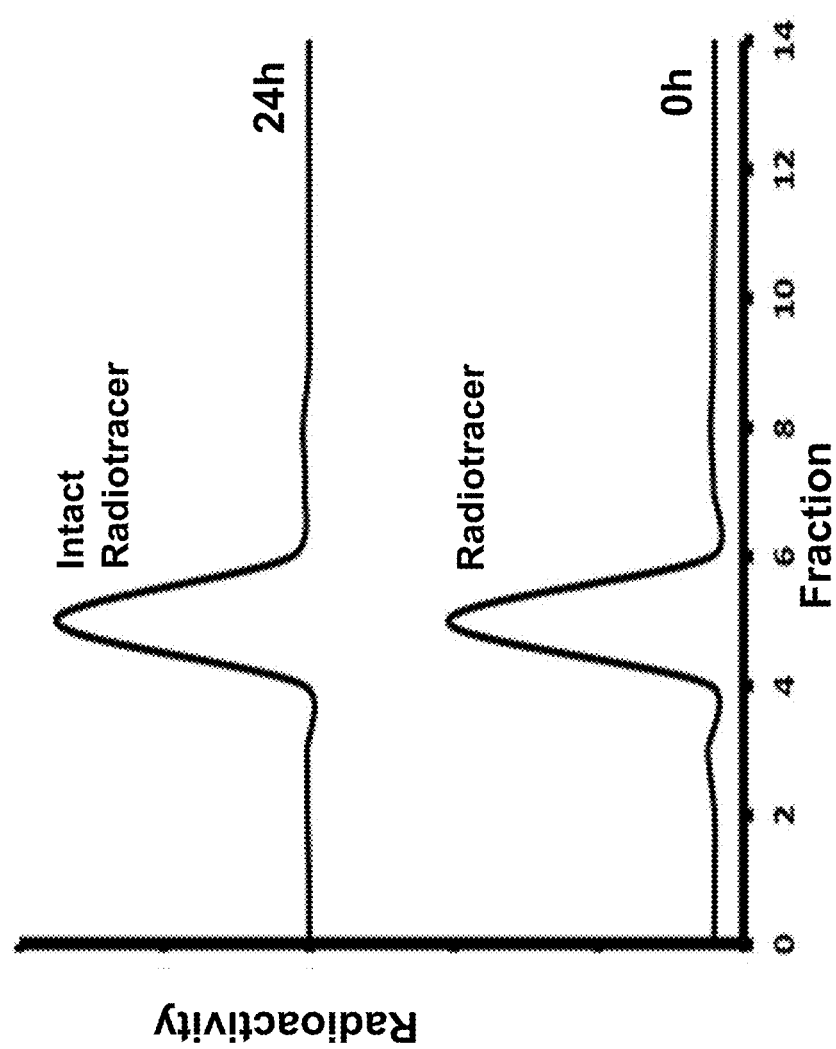

IMMUNO IMAGING AGENT FOR USE WITH ANTIBODY-DRUG CONJUGATE THERAPY

This application claims the benefit of U.S. Provisional Application No. 61/761,188, filed Feb. 5, 2013, the disclosure of which is explicitly incorporated by reference herein.

JOINT RESEARCH AGREEMENT

The present disclosure was made by or on behalf of the following parties to a joint research agreement: (1) The Board Of Trustees Of The Leland Stanford Junior University and (2) Sanofi U.S. Services Inc.

FIELD OF THE INVENTION

The invention relates to a companion diagnostic antibody-like binding protein and methods of use.

BACKGROUND OF THE INVENTION

There are a number of challenges in developing drugs for therapeutic use in a patient population. Many initial agents do not reach the market for any number of reasons (e.g., lack of clinical benefit or lack of proven safety in a patient population). Some critical issues for the development of effective and safe drugs are: (1) establishing that a drug interacts with its intended molecular target in a patient population; (2) establishing that the specific target is relevant to treating the particular disease in the same patient population; and (3) identifying a biologically optimal dose based on the drug's effect on the target in the same patient population. The development of an appropriate companion diagnostic for a particular drug helps significantly in developing a drug for use in a clinical patient population.

A companion diagnostic coupled with molecular imaging provides a powerful, non-invasive 4-dimensional assessment of a molecular target and its interaction with drug molecules in vivo. Some examples of imaging platforms includes: magnetic resonance imaging (MRI); positron emission tomography (PET); single photon emission tomography (SPECT); optical imaging, computed tomography (CT); ultrasound, X-ray or photoacoustic imaging. Selection of an imaging contrast takes into account the specific molecular probe and intrinsic tissue characteristics. The coupling of a companion diagnostic with molecular imaging allows for a better understanding of a particular drug's interaction with its molecular target in patients, which can help in identifying potential responders to the specific drug and aid in the understanding and determination of the mechanisms of sensitivity and resistance of the drug (and its optimal dosing).

SUMMARY OF THE INVENTION

A companion diagnostic antibody-like binding protein based on the humanized monoclonal antibody, DS6, was developed for use as a diagnostic tool for in vivo detection and quantification of the tumor-associated MUC1-sialoglycotope, CA6, by an imaging technique, such as positron emission tomography (PET) bio-imaging. The antibody-like binding protein facilitates patient stratification and early evaluation of the therapeutic efficacy of the humanized DS6 antibody-drug immunoconjugate, huDS6-DM4, which consists of a humanized monoclonal antibody against the tumor-associated MUC1-sialoglycotope, CA6, conjugated to the cytotoxic maytansinoid, DM4.

The companion diagnostic antibody-like binding protein can be used to identify patients and patient subpopulations with high CA6 expression who may preferentially respond to treatment with a drug that targets tissues (e.g., tumor tissues) having high CA6 expression, such as an antibody drug conjugate (ADC) that targets the CA6 epitope. The ADC can be, for example, an huDS6 molecule attached to a cytotoxic agent, such as a maytansine derivative, such as DM1 or DM4, or another agent such as described in the International Publication No. WO 2005/009369. The companion diagnostic antibody-like binding protein can be administered prior to the administration of the ADC, such as to determine whether the subject is likely to respond to treatment with the ADC.

The companion diagnostic antibody-like binding protein can be used for CA6 detection in vivo by a bio-imaging technique, such as positron emission tomography (PET), and allows for short exposure times and fast imaging, such as within 48 to 24 hours or less, the companion diagnostic is a highly specific binder with appropriate clearance kinetics.

The invention as disclosed herein provides an antibody-like binding protein that specifically binds CA6, wherein the antibody-like binding protein further comprises a chelator. The antibody-like binding protein can be used as a diagnostic tool for in vivo detection and quantification of the human CA6 tumor antigen by a bio-imaging technique, such as PET, wherein the antibody-like binding protein is conjugated to a suitable chelator for coupling to the bio-imaging tracer.

The invention as disclosed herein further provides an antibody-like binding protein that specifically binds CA6, wherein the antibody-like binding protein further comprises a chelator. The antibody-like binding protein can be used as an imaging or detection agent for tissue expressing the CA6 tumor antigen, wherein the antibody-like binding protein is conjugated to a suitable chelator for coupling to an agent.

The invention as disclosed herein further provides a method of making a DS6 antibody-like binding protein comprising respective $V_L$ and $V_H$ DNA sequences from humanized DS6 antibody arranged in tandem and separated by a linker sequence. The DS6 $V_L$-Linker-DS6 $V_L$ and DS6 $V_H$-Linker-DS6 $V_H$ constructs are fused on DNA level at the 3' end to human constant domain sequences, according to formulas [I] and [II] below:

$$V_{L1}\text{-}L_1\text{-}V_{L2}\text{-}C_L \quad [\text{I}]$$

$$V_{H1}\text{-}L_2\text{-}V_{H2}\text{-}C_{H1} \quad [\text{II}]$$

wherein:
$V_{L1}$ is a DS6-based immunoglobulin light chain variable domain;
$V_{L2}$ is a DS6-based immunoglobulin light chain variable domain;
$V_{H1}$ is a DS6-based immunoglobulin heavy chain variable domain;
$V_{H2}$ is a DS6-based immunoglobulin heavy chain variable domain;
$C_L$ is an immunoglobulin light chain constant domain, such as a human IGKC immunoglobulin light chain constant domain;
$C_{H1}$ is an immunoglobulin $C_{H1}$ heavy chain constant domain, such as a human immunoglobulin $C_{H1}$ heavy chain constant domain;
$L_1$ and $L_2$ are amino acid linkers; and
wherein the polypeptides of $V_{L1}$ and $V_{L2}$ are the same or different DS6-based immunoglobulin light chain variable domain, and the polypeptides of $V_{H1}$ and $V_{H2}$ are the same or different DS6-based immunoglobulin heavy chain variable domain; and wherein the polypeptides of formula I and the polypeptides of formula II form a bivalent monospecific tandem immunoglobulin antibody-like binding protein. The $C_L$ and $C_{H1}$ domains may be joined, such as by a disulfide bond. Furthermore, the polypeptides of formula I and formula II may comprise an optional tag (e.g., polyhistidine or 6×-His tag). The antibody-like binding protein in the methods of making a DS6 antibody-like binding protein disclosed herein may comprise any of the antibody-like binding proteins disclosed herein.

The invention as disclosed herein further provides a method of treating a disorder, such as a cancer in a patient, comprising the steps of obtaining the expression level of CA6 in the patient wherein an antibody-like binding protein that specifically binds CA6, wherein the antibody-like binding protein further comprises a chelator, is administered to the patient, and making a determination as to whether tissues are expressing CA6; and administering huDS6-DM4 to the patient if the patient has a CA6 expression level that is at least 10% greater than a CA6 expression level in a reference tissue, e.g., 10%, 20%, 30%, 40% or greater than CA6 expression in a reference tissue. In some embodiments, the antibody-like binding protein featured in the invention is used to determine the level of CA6 expression in a tumor tissue such as in a serous ovarian carcinoma, endometriod ovarian carcinoma, neoplasm of the uterine cervix, neoplasm of the endometrius, neoplasm of the vulva, breast carcinoma, pancreatic tumor, and tumor of the urothelium. The antibody-like binding protein in the methods of treating a disorder disclosed herein may comprise any of the antibody-like binding proteins disclosed herein.

The invention as disclosed herein further provides a method of determining whether a cancer patient is a candidate for treatment with huDS6-DM4, the method comprising the steps of obtaining the expression level of CA6 in the patient wherein an antibody-like binding protein that specifically binds CA6, wherein the antibody-like binding protein further comprises a chelator is administered to the patient, and making a determination as to whether the CA6 expression level is at least 10% greater than a CA6 expression level in a reference tissue, e.g., 10%, 20%, 30%, 40% or greater than CA6 expression in a reference tissue; and providing an indication that the cancer patient is a candidate for treatment with huDS6-DM4 when the determination is made in the affirmative. The antibody-like binding protein in the methods of determining whether a cancer patient is a candidate for treatment with huDS6-DM4 disclosed herein may comprise any of the antibody-like binding proteins disclosed herein.

The invention as disclosed herein further provides a method of monitoring a cancer patient's response to treatment with huDS6-DM4, the method comprising the steps of obtaining the expression level of CA6 in the patient, administering to the patient an antibody-like binding protein that specifically binds CA6, wherein the antibody-like binding protein further comprises a chelator, before and during treatment with huDS6-DM4, making a determination as to whether the CA6 expression level is increased, the same, or decreased as a result of treatment with huDS6-DM4; and providing an indication that treatment should be continued if the level of CA6 expression in the patient has decreased as compared to the level of CA6 expression before treatment with the huDS6-DM4. The antibody-like binding protein in the methods of monitoring a cancer patient's response to treatment with huDS6-DM4 disclosed herein may comprise any of the antibody-like binding proteins disclosed herein.

The invention provides an antibody-like binding protein that specifically binds CA6, wherein the antibody-like binding protein comprises two polypeptides having structures represented by the formulas [I] and [II] below:

$$V_{L1}\text{-}L_1\text{-}V_{L2}\text{-}C_L \qquad [I]$$

$$V_{H1}\text{-}L_2\text{-}V_{H2}\text{-}C_{H1} \qquad [II]$$

wherein:
$V_{L1}$ is a DS6-based immunoglobulin light chain variable domain;
$V_{L2}$ is a DS6-based immunoglobulin light chain variable domain;
$V_{H1}$ is a DS6-based immunoglobulin heavy chain variable domain;
$V_{H2}$ is a DS6-based immunoglobulin heavy chain variable domain;
$C_L$ is an immunoglobulin light chain constant domain, such as a human IGKC immunoglobulin light chain constant domain;
$C_{H1}$ is an immunoglobulin $C_{H1}$ heavy chain constant domain, such as a human immunoglobulin $C_{H1}$ heavy chain constant domain;
$L_1$ and $L_2$ are amino acid linkers;
wherein the polypeptides of formula I and the polypeptides of formula II form a bivalent monospecific tandem immunoglobulin antibody-like binding protein; and
wherein the antibody-like protein further comprises a chelator.

The invention also provides a method for making an antibody-like binding protein that specifically binds CA6, wherein the antibody-like binding protein further comprises a chelator, comprising:

(a) expressing in a cell one or more nucleic acid molecules encoding polypeptides having structures represented by the formulas [I] and [II] below:

$$V_{L1}\text{-}L_1\text{-}V_{L2}\text{-}C_L \qquad [I]$$

$$V_{H1}\text{-}L_2\text{-}V_{H2}\text{-}C_{H1} \qquad [II]$$

wherein:
$V_{L1}$ is a DS6-based immunoglobulin light chain variable domain;
$V_{L2}$ is a DS6-based immunoglobulin light chain variable domain;
$V_{H1}$ is a DS6-based immunoglobulin heavy chain variable domain;
$V_{H2}$ is a DS6-based immunoglobulin heavy chain variable domain;
$C_L$ is an immunoglobulin light chain constant domain, such as a human IGKC immunoglobulin light chain constant domain;
$C_{H1}$ is an immunoglobulin $C_{H1}$ heavy chain constant domain, such as a human immunoglobulin $C_{H1}$ heavy chain constant domain;
$L_1$ and $L_2$ are amino acid linkers; and
wherein the polypeptides of formula I and the polypeptides of formula II form a bivalent monospecific tandem immunoglobulin antibody-like binding protein; and (b) attaching the antibody-like binding protein to the chelator.

The invention further provides a method for treating diseased tissue expressing CA6 in a patient comprising administering an antibody-like binding protein that specifically binds CA6 and further comprises a chelator and an imaging agent to the patient; identifying the diseased tissue expressing CA6 in the patient by positron emission tomography (PET) imaging; and determining that the patient is a candidate for treatment with huDS6-DM4 if the CA6 expression in the diseased tissue is greater than or equal to 10% of CA6 expression in a reference standard. The antibody-like binding protein in the methods of treating a diseased tissue expressing CA6 in a patient disclosed herein may comprise any of the antibody-like binding proteins disclosed herein.

The invention further provides a method of treating CA6 positive cancer in a patient, comprising the steps of acquiring information regarding expression level of CA6 in the patient; and administering huDS6-DM4 to the patient if the expression level of CA6 in the patient is greater than or equal to 10% of CA6 expression in a reference standard. In some embodiments, the information regarding expression level of CA6 in the patient is acquired by administering an antibody-like protein that specifically binds CA6 and comprises a chelator and an imaging agent, and detecting the localization of the imaging agent in the patient using a bioimaging technique. In some embodiments, the antibody-like binding protein comprises any of the antibody-like binding proteins disclosed herein.

The invention further provides a method of determining whether a cancer patient is a candidate for treatment with huDS6-DM4, comprising the steps of acquiring information regarding expression level of CA6 in the patient; and determining that the patient is a candidate for treatment with huDS6-DM4 if the expression level of CA6 in the patient is greater than or equal to 10% of CA6 expression in a reference standard. In some embodiments, the information regarding expression level of CA6 in the patient is acquired by administering an antibody-like protein that specifically binds CA6 and comprises a chelator and an imaging agent, and detecting the localization of the imaging agent in the patient using a bioimaging technique. In some embodiments, the antibody-like binding protein comprises any of the antibody-like binding proteins disclosed herein.

The invention further provides a method of monitoring a cancer patient's response to treatment with huDS6-DM4, comprising the steps of acquiring information regarding expression level of CA6 in the patient following administration of the huDS6-DM4; and providing an indication that treatment should be continued if the level of CA6 expression in the patient has decreased as compared to the level of CA6 expression before treatment with the huDS6-DM4. In some embodiments, the information regarding expression level of CA6 in the patient is acquired by treating the patient with huDS6-DM4 for a prescribed period of time; administering an antibody-like protein that specifically binds CA6 and comprises a chelator and an imaging agent; and detecting the localization of the imaging agent in the patient using a bioimaging technique. In some embodiments, the antibody-like binding protein comprises any of the antibody-like binding proteins disclosed herein.

The invention provides an antibody-like binding protein that specifically binds CA6, wherein the antibody-like binding protein comprises two polypeptides having structures represented by the formulas [I] and [II] below:

$$V_{L1}\text{-}L_1\text{-}V_{L2}\text{-}C_L \qquad [\text{I}]$$

$$V_{H1}\text{-}L_2\text{-}V_{H2}\text{-}C_{H1} \qquad [\text{II}]$$

wherein:
$V_{L1}$ is a DS6-based immunoglobulin light chain variable domain;
$V_{L2}$ is a DS6-based immunoglobulin light chain variable domain;
$V_{H1}$ is a DS6-based immunoglobulin heavy chain variable domain;
$V_{H2}$ is a DS6-based immunoglobulin heavy chain variable domain;
$C_L$ is an immunoglobulin light chain constant domain, such as a human IGKC immunoglobulin light chain constant domain;
$C_{H1}$ is an immunoglobulin $C_{H1}$ heavy chain constant domain, such as a human immunoglobulin $C_{H1}$ heavy chain constant domain;
$L_1$ and $L_2$ are amino acid linkers; and
wherein the polypeptides of formula I and the polypeptides of formula II form a bivalent monospecific tandem immunoglobulin antibody-like binding protein.

The invention also provides a method for making an antibody-like binding protein that specifically binds CA6, comprising expressing in a cell one or more nucleic acid molecules encoding polypeptides having structures represented by the formulas [I] and [II] below:

$$V_{L1}\text{-}L_1\text{-}V_{L2}\text{-}C_L \qquad [\text{I}]$$

$$V_{H1}\text{-}L_2\text{-}V_{H2}\text{-}C_{H1} \qquad [\text{II}]$$

wherein:
$V_{L1}$ is a DS6-based immunoglobulin light chain variable domain;
$V_{L2}$ is a DS6-based immunoglobulin light chain variable domain;
$V_{H1}$ is a DS6-based immunoglobulin heavy chain variable domain;
$V_{H2}$ is a DS6-based immunoglobulin heavy chain variable domain;
$C_L$ is an immunoglobulin light chain constant domain, such as a human IGKC immunoglobulin light chain constant domain;
$C_{H1}$ is an immunoglobulin $C_{H1}$ heavy chain constant domain, such as a human immunoglobulin $C_{H1}$ heavy chain constant domain;
$L_1$ and $L_2$ are amino acid linkers; and
wherein the polypeptides of formula I and the polypeptides of formula II form a bivalent monospecific tandem immunoglobulin antibody-like binding protein.

Specific embodiments of the invention will become evident from the following more detailed description of certain embodiments and the claims.

DETAILED DESCRIPTION OF THE INVENTION

Figure 1:
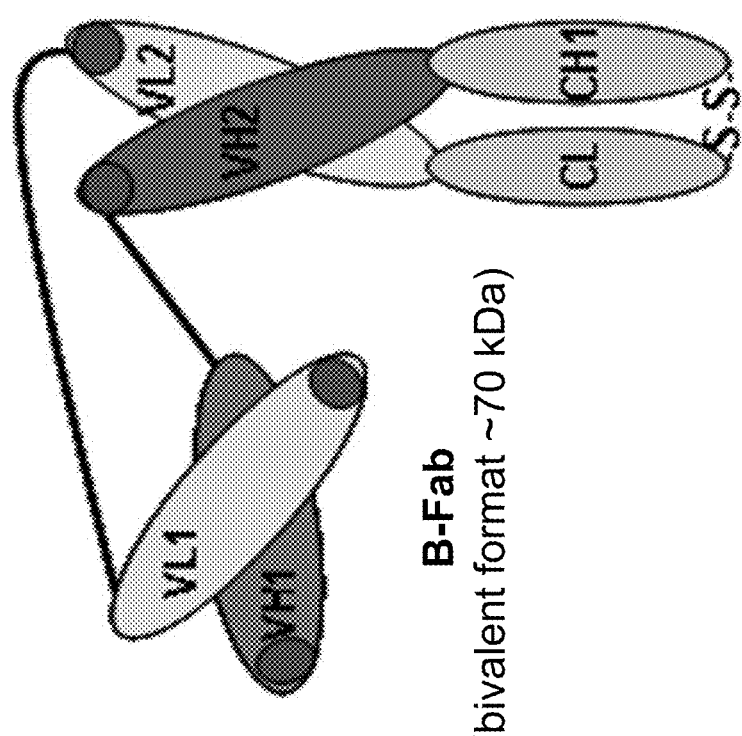
FIG. 1. Schematic representation of the bivalent engineered antibody-like binding protein, a bivalent monospecific tandem immunoglobulin fragment (B-Fab). Examples of B-Fab proteins include: B-Fab with G4SG4S linker (SEQ ID NO: 3) and C-terminal 6x-His tag, B-Fab with G4SG4S linker (SEQ ID NO: 3) without C-terminal 6x-His tag, and B-Fab with G4S linker and C-terminal 6x-His tag.

The invention as disclosed herein relates to a companion diagnostic antibody-like binding protein based on the humanized monoclonal antibody, DS6, to be used as diagnostic tool for in vivo detection and quantification of the human CA6 tumor antigen by PET bio-imaging. The companion diagnostic antibody-like binding protein will facilitate patient stratification and early evaluation of the therapeutic efficacy of the DS6 antibody-drug immunoconjugate huDS6-DM4 consisting of a humanized monoclonal antibody against the tumor-associated MUC1-sialoglycotope, CA6, conjugated to the cytotoxic maytansinoid, DM4. The antibody-drug immunoconjugate, huDS6-DM4, is described, for example, in International Publication No. WO 2005/009369, incorporated herein by reference. The DS6 antibody and the CA6 tumor antigen are described, for example, in Kearse et al. (Int J Cancer. 2000 Dec. 15; 88(6):866-72), incorporated herein by reference.

HuDS6-DM4 is a first in class antibody-drug immunoconjugate consisting of a humanized monoclonal antibody (huDS6) against the tumor-associated MUC1-sialoglycotope, CA6, conjugated to the cytotoxic maytansinoid, DM4. Mucin proteins play an essential role in forming protective mucous barriers on epithelial surfaces, and are expressed on the apical surface of epithelial cells that line the mucosal surfaces of many different tissues including lung, breast, ovarian stomach and pancreas. MUC1 (mucin-1) is known to be overexpressed in a number of epithelial cancers, and CA6 overexpression is linked to aggressive behavior in human cancers and poor patient outcome. CA6 has limited distribution among normal adult tissues, thus making the DS6 antibody a promising agent for the selective treatment CA6 positive tumors (e.g., tumors of the ovaries, uterus, pancreas, breast or lung). Upon antibody/antigen binding and internalization, the huDS6-DM4 immunoconjugate releases DM4, which binds to tubulin and disrupts microtubule assembly/disassembly dynamics, resulting in mitotic arrest of CA6-expressing tumor cells. HuDS6-DM4 is currently undergoing a phase I clinical trial in patients diagnosed with CA6 antigen positive solid tumors.

To identify patients who show expression of the CA6 in tumors and therefore may respond to the treatment with huDS6-DM4, a companion diagnostic tool that binds CA6 with high affinity was developed. Furthermore, this companion diagnostic antibody-like binding protein acts as an early efficacy marker providing an adjunct tool to non-invasively monitor a patient's response to huDS6-DM4 therapy thereby facilitating patient stratification in clinical trials or clinical treatment (i.e., a decrease in CA6 signal correlated to tumor shrinkage or target down-regulation coupled to insufficient efficacy). Such a companion diagnostic can reduce attrition and help deliver effective medicine to patients faster. The companion diagnostic antibody-like binding protein as disclosed herein can also be used for CA6 detection in vivo by PET bio-imaging. To allow for short exposure times and fast imaging, e.g., within 48 to 24 hours or less, with high tumor to blood signals, a highly specific binder with appropriate clearance kinetics was needed.

Different novel antibody-like binding proteins derived from the DS6 antibody sequence were developed along with a suitable chelator and radiolabel in order to meet the required specifications for PET imaging (e.g., better tumor penetration, faster clearance kinetics and excellent tumor to blood ratio). Based on pre-determined imaging figures of merit (IFOM), a ~70 kDa antibody fragment (a bivalent monospecific tandem immunoglobulin, termed B-Fab) was chosen for specificity evaluation and eventual clinical translation. The B-Fab format provided the advantages of: (1) high stability to heat stress (incubation at 42° C. for one week); (2) high stability in human serum (incubation at 37° C. for 24 h); and (3) reasonable productivity in transient cell culture (~2 mg/L). Compared to full-length antibodies (~150 kDa), antibody fragments (~50-75 kDa) show faster renal elimination rates and blood clearance, which results in higher signal to noise ratios during PET bio-imaging.

The B-Fab DS6 antibody-like binding protein contains two CA6 antigen recognition sites based on the CA6 antigen recognition sites of the DS6 humanized monoclonal antibody and shows high binding affinity to the CA6 antigen. After conjugation with a chelator (e.g., DOTA, NOTA, DTPA, TETA, or Df) the DS6 B-Fab was radiolabeled and used for in vivo PET bio-imaging experiments.

Standard recombinant DNA methodologies were used to construct the polynucleotides that encode the polypeptides which form the companion diagnostic antibody (based on the DS6 antibody) of the invention, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

1. General Definitions

As utilized in accordance with the present disclosure, the following terms, unless otherwise indicated, shall be understood to have the following meanings. Unless otherwise required by context, singular terms shall include pluralities and plural terms shall include the singular.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which by virtue of its origin the isolated polynucleotide: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

As used herein, the term "antibody" encompasses chimeric, humanized, human and murine antibodies.

The term "human antibody" as used herein includes antibodies having variable and constant regions substantially corresponding to human germline immunoglobulin sequences. In some embodiments, human antibodies are produced in non-human mammals, including, but not limited to, rodents, such as mice and rats, and lagomorphs, such as rabbits. In other embodiments, human antibodies are produced in hybridoma cells. In still other embodiments, human antibodies are produced recombinantly.

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Mammalian light chains, in particular human light chains, are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "native Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc" as used herein is generic to the monomeric, dimeric, and multimeric forms.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

The term "antibody-like binding protein" as used herein refers to a non-naturally occurring (or recombinant) engineered molecule that specifically binds to at least one target antigen. It encompasses, e.g., F(ab) fragment, F(ab') fragments and diabodies.

In certain aspects, the "antibody-like binding protein" comprises the respective $V_L$ and $V_H$ DNA sequences from an antibody arranged in tandem and separated by a short amino acid linker sequence, according to formulas [I] and [II] below:

$$V_{L1}\text{-}L_1\text{-}V_{L2}\text{-}C_L \quad [\text{I}]$$

$$V_{H1}\text{-}L_2\text{-}V_{H2}\text{-}C_{H1} \quad [\text{II}]$$

wherein:
$V_{L1}$ is an immunoglobulin light chain variable domain;
$V_{L2}$ is an immunoglobulin light chain variable domain;
$V_{H1}$ is an immunoglobulin heavy chain variable domain;
$V_{H2}$ is an immunoglobulin heavy chain variable domain;
$C_L$ is an immunoglobulin light chain constant domain;
$C_{H1}$ is an immunoglobulin $C_{H1}$ heavy chain constant domain;
$L_1$ and $L_2$ are amino acid linkers; and
wherein the polypeptides of formula I and the polypeptides of formula II form a Fab fragment (bivalent monospecific tandem immunoglobulin fragment).

In certain aspects, $V_{L1}$ and $V_{L2}$ are identical polypeptides, and in certain aspects $V_{H1}$ and $V_{H2}$ are identical polypeptides.

In certain aspects, each of $L_1$ and $L_2$ has a length of at least 5, 6, 7, 8, 9 or 10 amino acids.

In certain aspects, or typically, the $C_L$ and $C_{H1}$ domains are linked by a disulfide bond.

In certain aspects, each of $L_1$ and $L_2$ is either GGGGS or GGGGSGGGGS (SEQ ID NO: 3).

In certain aspects, the polypeptide of formula [I] comprises a sequence at least 80%, 85%, 90%, 95%, 96%, 97%, 98%, 99% or 100% identical to SEQ ID NO: 1.

In certain aspects, the polypeptide of formula [II] comprises a sequence at least 80%, 85%, 90%, 95%, 96%, 97%, 98%, 99% or 100% identical to SEQ ID NO: 7.

In certain aspects, said antibody-like binding protein further comprises at least one radiolabel, imaging agent, therapeutic agent, or diagnostic agent.

In certain aspects, said antibody-like binding protein has a specific activity of at least 1, 1.1, 1.2, 1.3, 1.4 or 1.5 Ci/μMole.

In certain aspects, said antibody-like binding protein can have an apparent Kd of at most 8, 7, 6, 5 or 4 nM when the binding is measured by FACS, e.g. with a free antibody-like binding protein.

In certain aspects, said antibody-like binding protein presents a high stability to heat stress. More specifically, less than 25, 20, 15, 10 or 5% of soluble antibody-like binding protein can be lost after incubation at 42° C. for one week.

In certain aspects, said antibody-like binding protein presents a high stability in human serum. More specifically, at least 70, 75, 80, 85, 90 or 95% of the antibody-like binding protein can be monomeric after incubation at 37° C. for 24 hours in human serum.

An "isolated" antibody-like binding protein is one that has been identified and separated and/or recovered from a component of its natural environment. Contaminant components of its natural environment are materials that would interfere with diagnostic or therapeutic uses for the antibody-like binding protein, and may include enzymes, hormones, and other proteinaceous or non-proteinaceous solutes. In preferred embodiments, the antibody-like binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody-like binding proteins include the antibody-like binding protein in situ within recombinant cells since at least one component of the antibody-like binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The term "antigen" or "target antigen" as used herein refers to a molecule or a portion of a molecule that is capable of being bound by an antibody or antibody-like binding protein, and additionally is capable of being used in an animal to produce antibodies capable of binding to an epitope of that antigen. A target antigen may have one or more epitopes. With respect to each target antigen recognized by an antibody-like binding protein, the antibody-like binding protein is capable of competing with an intact antibody that recognizes the target antigen. A "bivalent" antibody-like binding protein, other than a "multispecific" or "multifunctional" antibody-like binding protein, is understood to comprise antigen binding sites having identical antigenic specificity.

A bispecific or bifunctional antibody typically is an artificial hybrid antibody having two different heavy chain/light chain pairs and two different binding sites or epitopes. Bispecific antibodies may be produced by a variety of methods including, but not limited to, fusion of hybridomas or linking of F(ab') fragments.

An F(ab) fragment, also referred to as Fab, typically includes one light chain and the $V_H$ and $C_{H1}$ domains of one heavy chain, wherein the $V_H$-$C_{H1}$ heavy chain portion of the F(ab) fragment cannot form a disulfide bond with another heavy chain polypeptide. As used herein, an F(ab) fragment can also include one light chain containing two variable domains separated by an amino acid linker and one heavy chain containing two variable domains separated by an amino acid linker and a $C_{H1}$ domain. An F(ab) fragment can also include disulfide bond between the $C_L$ and $C_{H1}$.

An F(ab') fragment typically includes one light chain and a portion of one heavy chain that contains more of the constant region (between the $C_{H1}$ and $C_{H2}$ domains), such that an interchain disulfide bond can be formed between two heavy chains to form an F(ab)$_2$ molecule.

A "diabody" typically is a dimer of two single-chain variable fragments (scFv) that each consist of the heavy chain variable ($V_H$) and light chain variable ($V_L$) regions connected by a small peptide linker that is too short for the two variable regions to fold together, forcing scFvs to dimerize.

The phrases "biological property," "biological characteristic," and the term "activity" in reference to an antibody-like binding protein of the invention are used interchangeably herein and include, but are not limited to, epitope affinity and specificity, ability to antagonize the activity of the antigen target (or targeted polypeptide), the in vivo stability of the antibody-like binding protein, and the immunogenic properties of the antibody-like binding protein. Other identifiable biological properties or characteristics of an antibody-like binding protein include, for example, cross-reactivity, (i.e., with non-human homologs of the antigen target, or with other antigen targets or tissues, generally), and ability to preserve high expression levels of protein in mammalian cells. The aforementioned properties or characteristics can be observed or measured using art-recognized techniques including, but not limited to ELISA, competitive ELISA, surface plasmon resonance analysis, in vitro and in vivo neutralization assays, and immunohistochemistry with tissue sections from different sources including human, primate, or any other source as the need may be.

The term "immunologically functional immunoglobulin fragment" as used herein refers to a polypeptide fragment that contains at least the CDRs of the immunoglobulin heavy or light chains from which the polypeptide fragment was derived. An immunologically functional immunoglobulin fragment is capable of binding to a target antigen.

A "neutralizing" antibody-like binding protein as used herein refers to a molecule that is able to block or substantially reduce an effector function of a target antigen to which it binds. As used herein, "substantially reduce" means at least about 60%, preferably at least about 70%, more preferably at least about 75%, even more preferably at least about 80%, still more preferably at least about 85%, most preferably at least about 90% reduction of an effector function of the target antigen.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or antibody-like binding protein. In certain embodiments, an antibody-like binding protein is said to specifically bind an antigen when it preferentially recognizes its target antigen in a complex mixture of proteins and/or macromolecules. In preferred embodiments, an antibody-like binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of an antibody-like binding protein can be determined, for example, by surface plasmon resonance. Generally, surface plasmon resonance analysis measures real-time binding interactions between ligand (a target antigen on a biosensor matrix) and analyte (an antibody-like binding protein in solution) by surface plasmon resonance (SPR) using the BIAcore system (Pharmacia Biosensor; Piscataway, N.J.). Surface plasmon analysis can also be performed by immobilizing the analyte (antibody-like binding protein on a biosensor matrix) and presenting the ligand (target antigen). The term "$K_D$," as used herein refers to the dissociation constant of the interaction between a particular antibody-like binding protein and a target antigen.

The term "specifically binds" as used herein refers to the ability of an antibody-like binding protein or an antigen-binding fragment thereof to bind to an antigen containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen.

The term "linker" as used herein refers to one or more amino acid residues inserted between immunoglobulin domains to provide sufficient mobility for the domains of the light and heavy chains to fold into cross over dual variable region immunoglobulins. Non-limiting examples include glycine/serine linkers, such as GGGGS or GGGGSGGGGS (SEQ ID NO: 3), and glycine/alanine linkers. A linker is inserted at the transition between variable domains or between variable and constant domains, respectively, at the sequence level. The transition between domains can be identified because the approximate sizes of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers are independent, but they may in some cases have the same sequence and/or length. Exemplary amino acid linkers are known in the art and are suitable for the uses described herein.

The term "tag" as used herein refers to any linked molecule or affinity based sequence fused, usually in-frame, at any position (typically the N-terminal or C-terminal end) of a polypeptide or antibody-like binding protein. The presence of a suitable tag may serve to improve detection, purification or other characteristics of the antibody-like protein. Suitable affinity based tags include any sequence that may be specifically bound to another moiety (non-limiting examples include poly-histidine, 6×-histidine, FLAG, V5, biotin, HA, GST or MBP). In some instances, a linked molecule may be a light emitting reporter that may include any domain that can report the presence of a polypeptide. Suitable light emitting reporter domains include luciferase, fluorescent proteins or light emitting variants thereof.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the invention is intended to include other forms of expression vectors, such as viral vectors (e.g., replication defective retroviruses, adenoviruses, and adeno-associated viruses), which serve equivalent functions.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription, and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the antibody-like binding proteins of the invention, including bacterial, yeast, baculoviral, and mammalian expression systems (as well as phage display expression systems). An example of a suitable bacterial expression vector is pUC19. To express an antibody-like binding protein recombinantly, a host cell is transformed or transfected with one or more recombinant expression vectors carrying DNA fragments encoding the polypeptide chains of the antibody-like binding protein such that the polypeptide chains are expressed in the host cell and, preferably, secreted into the medium in which the host cells are cultured, from which medium the antibody-like binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids such as $\alpha$-,$\alpha$-disubstituted amino acids, N-alkyl amino acids, lactic acid, and other unconventional amino acids may also be suitable components for the polypeptide chains of the antibody-like binding proteins of the invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
(1) hydrophobic: Met, Ala, Val, Leu, Ile, Phe, Trp, Tyr, Pro;
(2) polar hydrophilic: Arg, Asn, Asp, Gln, Glu, His, Lys, Ser, Thr;
(3) aliphatic: Ala, Gly, Ile, Leu, Val, Pro;
(4) aliphatic hydrophobic: Ala, Ile, Leu, Val, Pro;
(5) neutral hydrophilic: Cys, Ser, Thr, Asn, Gln;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid residues. Non-conservative substitutions may involve the exchange of a member of one of these classes for a member from another class.

A skilled artisan will be able to determine suitable variants of the polypeptide chains of the antibody-like binding proteins of the invention using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "chelator" is chemical compound in the form of a heterocyclic ring that can contain a metal coordinated to at least two nonmetal ions. The presence of hard acid cation chelate moieties on the antibody-like binding protein helps to ensure rapid in vivo clearance of the companion diagnostic.

Chelators are covalently bound to the antibody or antibody-like binding protein using standard methods of bioconjugation. Amine containing residues (e.g., lysine or N-terminus) on the antibody undergo amide bond formation with a chelator containing an activated ester (e.g., an N-hydroxysuccinimidyl ester). Sulfur containing residues (e.g., cysteine) undergo conjugation with chelators containing an activated ester or maleimide moiety. Alternatively, bioconjugates are formed when activated carboxylate residues on the antibody undergo amide or thioester formation with amine or thiol groups, respectively, on the chelator. Bifunctional linkers, such as, for example, PEG-maleimide (PEG-Mal), succinimidyl-4-(N-maleimidomethyl)cyclohexane-1-carboxylate (SMCC) or N-succinimidyl 3-(2-pyridylthio) propionate (SPDP) are used where necessary.

Chelators are chosen for their metal-binding properties, and may be changed at will. Chelators such as NOTA (1,4,7-triaza-cyclononane-N,N',N"-triacetic acid), DOTA (1,4,7,10-tetraazacyclododecane-1,4,7,10-tetraacetic acid), DTPA (1,1,4,7,7-Diethylenetriaminepentaacetic acid), TETA (p-bromoacetamido-benzyl-tetraethylaminetetraacetic acid), and Df (desferrioxamine B) are of use with a variety of radiolabels, radionuclides, radioisotopes, metals and radiometals. DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Also, more than one type of chelator may be conjugated to the targetable construct to bind multiple metal ions, e.g., diagnostic radionuclides and/or therapeutic radionuclides.

Particularly useful diagnostic radiolabels, radionuclides or radioisotopes that can be bound to the chelating agents of the antibody or engineered antibody-like binding protein include, but are not limited to, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. The diagnostic radiolabels include a decay energy in the range of 25 to 10,000 keV, more preferably in the range of 25 to 4,000 keV, and even more preferably in the range of 20 to 1,000 keV, and still more preferably in the range of 70 to 700 keV. Total decay energies of useful positron-emitting radionuclides are preferably <2,000 keV, more preferably under 1,000 keV, and most preferably <700 keV. Radiolabels useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radiolabels are preferably 20 to 2000 keV, more preferably 60 to 600 keV, and most preferably 100 to 300 keV.

The term "patient" as used herein includes, but is not limited to human and animal subjects.

A "disorder" is any condition that would benefit from treatment using the antibody or engineered antibody-like binding protein of the invention. "Disorder" and "condition" are used interchangeably herein and include chronic and acute disorders or diseases, including those pathological conditions that predispose a patient to the disorder in question. In certain aspects, the disorder is cancer, such as a solid tumor cancer. In certain specific aspects, the cancer is breast cancer, colon cancer, ovarian carcinoma, endometrial cancer, osteosarcoma, cervical cancer, prostate cancer, lung cancer, synovial carcinoma, pancreatic cancer, kidney cancer, a cancer of the lymphatic system, a sarcoma or a carcinoma in which CA6 is expressed or other cancer yet to be determined in which CA6 glycotope is expressed predominantly. The cancer can be, for example, serous ovarian carcinoma, endometriod ovarian carcinoma, neoplasm of the uterine cervix, neoplasm of the endometrius, neoplasm of the vulva, breast carcinoma, pancreatic tumor, and tumor of the urothelium.

Any disorder that can be treated by the killing of selected cell populations is suitable for use with the antibody-like binding proteins described herein, such as a cancer, an autoimmune disease, such as systemic lupus, rheumatoid arthritis, and multiple sclerosis; a graft rejection, such as renal transplant rejection, liver transplant rejection, lung transplant rejection, cardiac transplant rejection, and bone marrow transplant rejection; graft versus host disease; viral infection, such as mV infection, HIV infection, AIDS, etc.; and parasite infection, such as giardiasis, amoebiasis, schistosomiasis, and others as determined by one of ordinary skill in the art.

A reference expression level can be, for example, the level of CA6 expression in undiseased tissue of the patient (e.g., from the same tissue-type as that containing the tumor), or the reference standard can be, for example, determined from an art-accepted standard, such as derived from expression levels in undiseased tissues from a population of individuals.

The terms "treatment" or "treat" as used herein refer to both therapeutic treatment and prophylactic or preventative measures. Those in need of treatment include those having the disorder as well as those prone to have the disorder or those in which the disorder is to be prevented.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of an antibody or engineered antibody-like binding protein.

The terms "effective amount" and "therapeutically effective amount" when used in reference to a pharmaceutical composition comprising one or more antibodies or engineered antibody-like binding proteins refers to an amount or dosage sufficient to produce a desired therapeutic result. More specifically, a therapeutically effective amount is an amount of an antibody or engineered antibody-like binding protein sufficient to inhibit, for some period of time, one or more of the clinically defined pathological processes associated with the condition being treated. As used herein, "therapeutically effective amount" also refers to an amount of antibody-like protein effective to visualize a CA6-expressing tissue, e.g., tumor tissue. The effective amount may vary depending on the specific antibody or engineered antibody-like binding protein that is being used, and also depends on a variety of factors and conditions related to the patient being treated and the severity of the disorder. For example, if the antibody or engineered antibody-like binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

The terms "acquire" or "acquiring" as used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis").

Information that is acquired indirectly can be provided in the form of a report, e.g., supplied in paper or electronic form, such as from an online database or application (an "App"). The report or information can be provided by, for example, a healthcare institution, such as a hospital or clinic; or a healthcare provider, such as a doctor or nurse.

One embodiment of the invention provides a pharmaceutical composition comprising a pharmaceutically acceptable carrier and a therapeutically effective amount of an antibody or engineered antibody-like binding protein.

2. Uses for Antibody-Like Binding Proteins

The antibody or engineered antibody-like binding proteins of the invention can be employed in any known assay method, such as competitive binding assays, direct and indirect sandwich assays, and immunoprecipitation assays for the detection and quantitation of one or more target antigens. The antibody or engineered antibody-like binding proteins will bind the one or more target antigens with an affinity that is appropriate for the assay method being employed.

For diagnostic applications, in certain embodiments, engineered antibody-like binding proteins can be labeled with a detectable moiety. The detectable moiety can be any one that is capable of producing, either directly or indirectly, a detectable signal. For example, the detectable moiety can be a radiolabel, radioisotope, radionuclide, imaging agent, therapeutic agent or diagnostic agent, such as $^{3}H$, $^{14}C$, $^{32}P$, $^{35}S$, $^{125}I$, $^{99}Tc$, $^{111}In$, $^{18}F$, $^{11}C$, $^{68}Ga$, $^{64}Cu$, $^{89}Zr$, $^{124}I$ or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase.

A proper reporter moiety can be detected by a particular imaging technique (e.g., $^{18}F/^{11}C/^{68}Ga/^{64}Cu/^{89}Zr/^{124}I$ radiolabeled reporter for PET imaging, $^{99m}Tc/^{111}In$ labeled reporter for SPECT imaging, a fluorescent dye labeled reporter for optical imaging or paramagnetic material labeled reporter for MRI). An appropriate match is recommended between the biologic half-life of an antibody or antibody-like binding protein and the physical half-life of the radiolabel (see Table 1).

TABLE 1

Examples of radiolabels and their half-life

| Radiolabel | Half-life |
|---|---|
| $^{68}Ga$ | 68 min |
| $^{18}F$ | 109 min |
| $^{64}Cu$ | 12.7 hr |
| $^{89}Zr$ | 78.4 hr |
| $^{124}I$ | 100.2 hr |

The development of an imaging companion diagnostic probe or antibody-like binding protein essentially requires a process similar to drug discovery (e.g., starting with target probe, radiation dosimetry, good laboratory practices toxicity studies, good manufacturing practice production, preclinical assessment, preclinical validation of target probe and clinical assessment). Additional parameters to be evaluated are: optimal timing of imaging relative to tracer administration, correlation with ex vivo analysis, tracer biodistribution and target specificity (tested with a radiolabeled non relevant fragment). Once fully developed, a molecular imaging probe can be used as a molecular imaging companion diagnostic for a particular drug or agent.

The engineered antibody-like binding proteins of the invention are also useful for in vivo imaging. An antibody-like binding protein labeled with a detectable moiety can be administered to an animal, preferably into the bloodstream, and the presence and location of the labeled antibody in the host assayed. The antibody-like binding protein can be labeled with any moiety that is detectable in an animal, whether by nuclear magnetic resonance, positron emission tomography or other detection means known in the art.

The in vivo imaging technique can be used to image a tissue, such as tumor tissue, to assess the level of CA6 glycotope expression in the tissue. Determining the level of CA6 expression in the tissue is useful, for example, to determine whether a patient, such as a cancer patient, will be a good candidate for treatment with a drug that targets a CA6 glycotope. For example, the antibody-like binding protein is useful as a companion diagnostic for a huDM6-DM4 cytotoxic agent.

In one embodiment, a patient is evaluated for treatment with a CA6 targeting molecule such as huDM6-DM4. The patient is evaluated, for example, by acquiring information regarding the level of CA6 expression in a diseased tissue, such as a tumor tissue (e.g., a tissue biopsy), and if the level of CA6 expression is determined to be greater than 10% of a reference expression level (e.g., greater than or equal to 10%, 20%, 30%, 40% or more than a reference level), then the patient is determined to be a good candidate for treatment with the CA6-targeting molecule. A patient who is a good candidate for treatment with the CA6-targeting molecule is predicted to respond positively to treatment with the molecule. A patient who does not have a suitable level of CA6 expression, e.g., less than 10% CA6 expression as compared to a reference standard, is determined not to be a good candidate for treatment with a CA6-targeting molecule.

A reference expression level can be, for example, the level of CA6 expression in undiseased tissue of the patient (e.g., from the same tissue-type as that containing the tumor), or the reference standard can be, for example, determined from an art-accepted standard, such as derived from expression levels in undiseased tissues from a population of individuals.

In one embodiment, the level of CA6 expression in a tissue of a subject is acquired indirectly, such as from a service-provider, such as from a medical institution, such as a hospital or clinic or doctor's office, or from a healthcare professional, such as a doctor or nurse, or from an insurance provider, or from a database. In another embodiment, the level of CA6 expression is determined directly, such as be administering the antibody-like binding protein featured in the invention to the subject, and determining the level of CA6 expression by a bioimaging technique.

A patient determined to be a good candidate for treatment with a CA6-targeting molecule can optionally be further administered the CA6-targeting molecule. In some embodiments, a patient treated with a CA6 targeting molecule will be monitored at intervals (e.g., weekly, biweekly, monthly, bimonthly) following administration of the CA6 targeting molecule to determine if the CA6 expression level is changing (e.g., decreasing) following treatment with the CA6 targeting molecule. If after a certain amount of time, or after the patient presents with adverse events, if the CA6 expression level in the diseased tissue remains unchanged, a decision can be made to stop or continue treatment with the CA6-targeting molecule.

In one embodiment, a patient is monitored during treatment with a CA6 targeting molecule such as huDM6-DM4. The patient is monitored, for example, by acquiring information regarding the level of CA6 expression in a diseased tissue, such as a tumor tissue, following administration of a CA6 targeting molecule or treatment with a CA6 targeting molecule such as huDM6-DM4, and if the level of CA6 expression is determined to be greater than 10% of a reference expression level (e.g., greater than or equal to 10%, 20%, 30%, 40% or more than a reference level), then the patient is determined to be a good candidate for continued treatment with the CA6-targeting molecule. If the level of CA6 expression is determined to have decreased during treatment with a CA6 targeting molecule such as huDM6-DM4, then the patient is determined to have responded positively to treatment with the molecule and treatment with huDS6-DM4 should continue. A patient who does not have a suitable level of CA6 expression, e.g., less than 10% CA6 expression as compared to a reference standard or who has an increased level of CA6 expression, is determined not to be a good candidate for continued treatment with a CA6-targeting molecule.

The invention as disclosed herein also relates to a kit comprising an antibody-like binding protein and other reagents useful for detecting target antigen levels in biological samples. Such reagents can include a detectable label, blocking serum, positive and negative control samples, and detection reagents.

4. Engineered Antibody-Like Binding Protein Compositions and Administration Thereof Compositions comprising engineered antibody-like binding proteins are within the scope of the invention. Such diagnostic, therapeutic or pharmaceutical compositions can comprise a diagnostic or therapeutically effective amount of an antibody-like binding protein, or antibody-like binding protein-drug conjugate, in admixture with a pharmaceutically or physiologically acceptable formulation agent selected for suitability with the mode of administration.

Acceptable formulation materials preferably are nontoxic to recipients at the dosages and concentrations employed.

The diagnostic or pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogensulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal diagnostic or pharmaceutical composition will be determined by a skilled artisan depending upon, for example, the intended route of administration, delivery format, and desired dosage. Such compositions can influence the physical state, stability, rate of in vivo release, and rate of in vivo clearance of the antibody-like binding protein.

The primary vehicle or carrier in a diagnostic or pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the invention, engineered antibody-like binding protein compositions can be prepared for storage by mixing the selected composition having the desired degree of purity with optional formulation agents in the form of a lyophilized cake or an aqueous solution. Further, the antibody-like binding proteins can be formulated as a lyophilizate using appropriate excipients such as sucrose.

The diagnostic or pharmaceutical compositions of the invention can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the diagnostic or therapeutic compositions for use in this invention can be in the form of a pyrogen-free, parenterally acceptable, aqueous solution comprising the desired antibody-like binding protein in a pharmaceutically acceptable vehicle. A particularly suitable vehicle for parenteral injection is sterile distilled water in which an antibody-like binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a diagnostic or pharmaceutical composition can be formulated for inhalation. For example, an antibody or engineered antibody-like binding protein can be formulated as a dry powder for inhalation. Antibody-like binding proteins inhalation solutions can also be formulated with a propellant for aerosol delivery. In yet another embodiment, solutions can be nebulized.

It is also contemplated that certain formulations can be administered orally. In one embodiment of the invention, antibody-like binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the antibody-like binding protein. Diluents, flavorings, low melting point waxes, vegetable oils, lubricants, suspending agents, tablet disintegrating agents, and binders can also be employed.

Another diagnostic or pharmaceutical composition can involve an effective quantity of antibody-like binding protein in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional diagnostic or pharmaceutical compositions of the invention will be evident to those skilled in the art, including formulations involving antibody-like binding protein in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D (−)-3-hydroxybutyric acid. Sustained-release compositions can also include liposomes, which can be prepared by any of several methods known in the art.

Diagnostic or pharmaceutical compositions of the invention to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the diagnostic or pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The invention also encompasses kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

EXAMPLES

The Examples that follow are illustrative of specific embodiments of the invention, and various uses thereof. They are set forth for explanatory purposes only, and should not be construed as limiting the scope of the invention in any way.

Example 1: Radiolabeling and In Vitro Characterization of Humanized DS6 Monoclonal Antibody and DS6-DM4

A clinically useful molecular imaging agent produces high contrast images within a reasonable amount of time following administration, demonstrates tumor penetration, has faster clearance kinetics and exhibits an excellent tumor to blood ratio. A caveat of using intact native antibodies in bioimaging is inherently slow kinetics of tumor uptake and blood clearance; they also tend to have high background and require a long time (hours to days) to obtain clear images of the tumor.

It has been previously shown that a radiolabeled tracer combined with bio-imaging can translate from a preclinical tumor model to a clinical setting (Williams et al., 2008, *Cancer Biother and Radiopharm* 23(6):797; Liu et al., (2009) *Mol Imaging Biol* 12:530). We further demonstrated that a radiolabeled DS6 antibody and DS6-DM4 effectively targeted WISH xenograft tumors in mice. Based on these results, three engineered antibody-like binding proteins were developed for optimized pharmacokinetics as an imaging based companion diagnostic.

Example 2: Expression of DS6 Engineered B-Fab

The expression plasmids encoding the heavy and light chains of the corresponding constructs were propagated in *E. coli* DH5α cells. Plasmids used for transfection were prepared from *E. coli* using the Qiagen EndoFree Plasmid Mega Kit (polypeptide and DNA sequences for the B-Fab antibody-like binding protein are in Table 2).

The DS6 antibody-like binding protein B-Fab was produced by transient transfection of HEK293 cells in FreeStyle F17 medium (Invitrogen). After 7 days after transfection, supernatant was harvested, and subjected to centrifugation and 0.2 μm filtration to remove particles. Purification was carried out by capture on KappaSelect (GE Healthcare). After binding the KappaSelect column, the column was washed with PBS or HEPES buffer (50 mM HEPES, 150 mM NaCl, pH 7.2, FP12016) followed by elution with 0.1M Glycin (pH 2.5) and neutralization with 1M Tris/HCl pH 9. The purification polishing step consisted of size exclusion chromatography using Superdex 200 (GE Healthcare) with PBS or HEPES buffer (50 mM HEPES, 150 mM NaCl, pH 7.2, FP12016). Following the polishing step, the purification product was concentrated by ultrafiltration, and finally the DS6 B-Fab was sterile filtered using a 0.22 μm membrane.

Protein concentration was determined by measurement of absorbance at 280 nm. Each batch was analyzed by SDS-PAGE under reducing and non-reducing conditions to determine the purity and molecular weight of each subunit and of the monomer. The quality of purified DS6 B-Fab was checked by the analytical methods described below.

TABLE 2

Polypeptide and DNA sequences for DS6 based B-Fab

| | |
|---|---|
| Amino acid sequence for:<br>$V_{L1}$-$L_1$-$V_{L2}$-$C_L$<br>(SEQ ID NO: 1) | EIVLTQSPATMSASPGERVTITCSAHSSVSFMHWFQQKPGTSPKLWIY<br>STSSLASGVPARFGGSGSGTSYSLTISSMEAEDAATYYCQQRSSFPLT<br>FGAGTKLELKGGGGSGGGGSEIVLTQSPATMSASPGERVTITCSAHSS<br>VSFMHWFQQKPGTSPKLWIYSTSSLASGVPARFGGSGSGTSYSLTISS<br>MEAEDAATYYCQQRSSFPLTFGAGTKLELKRTVAAPSVFIFPPSDEQL<br>KSGTASVVCLLNNFYPREAKVQWKVDNALQSGNSQESVTEQDSKDSTY<br>SLSSTLTLSKADYEKHKVYACEVTHQGLSSPVTKSFNRGEC |
| Amino acid sequence for:<br>Anti-CA6 $V_{L1}$<br>(SEQ ID NO: 2) | EIVLTQSPATMSASPGERVTITCSAHSSVSFMHWFQQKPGTSPKLWIY<br>STSSLASGVPARFGGSGSGTSYSLTISSMEAEDAATYYCQQRSSFPLT<br>FGAGTKLELK |
| Amino acid sequence for:<br>$L_1$ Linker<br>(SEQ ID NO: 3) | GGGGSGGGGS |
| Amino acid sequence for:<br>Anti-CA6 $V_{L2}$<br>(SEQ ID NO: 2) | EIVLTQSPATMSASPGERVTITCSAHSSVSFMHWFQQKPGTSPKLWIY<br>STSSLASGVPARFGGSGSGTSYSLTISSMEAEDAATYYCQQRSSFPLT<br>FGAGTKLELK |
| Amino acid sequence for:<br>$C_L$ Human IGKC<br>(SEQ ID NO: 4) | RTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSS<br>PVTKSFNRGEC |
| DNA coding sequence for:<br>$V_{L1}$-$L_1$-$V_{L2}$-$C_L$<br>(SEQ ID NO: 5) | gaaatcgtgctgacccagagccccgccaccatgtctgccagccctggc<br>gagagagtcaecatcacctgtagcgcccacagcagcgtcagtttcatg<br>cactggttccagcagaagcccggcaccagcccaaagctgtggatctac<br>agcaccagcagcctcgccagcggcgtcccagctcgctttggcggcagc<br>ggctctggcaccagctacagcctgaccatcagcagcatggaagccgag<br>gacgccgccacctactactgccagcagcggagcagctttcccctgacc<br>ttcggcgctggcaccaagctggaactgaagggcggaggcggatccggc<br>ggcggaggctccgagattgtgctgacacagtctccagccaccatgagc<br>gcctcccaggcgagcgcgtgacaatcacatgctccgcccactcctcc<br>gtgtcttttatgcattggtttcagcagaaacctgggacatcccctaaa<br>ctctggatctactccacctcctccctggcctccggggtgcccgctaga<br>tttggaggctctggcagcggcacctcctactccctgaccatctcctct<br>atggaagctgaagatgctgcaacatattattgccagcagagaagctcc<br>ttcccactgacatttggggccggaacaaagctcgagctgaagcgtacg<br>gtggccgctccttccgtgttcaicttccctccctccgacgagcagctg<br>aagtccggcaccgcctccgtggtgtgtctgctgaacaacttctaccct<br>cgggaggccaaggtgcagtggaaggtggacaacgccctgcagtccggc<br>aactcccaggagtccgtcaccgagcaggactccaaggacagcacctac<br>tccctgtcctccaccctgaccctgtccaaggccgactacgagaagcac<br>aaggtgtacgcctgtgaggtgacccaccagggcctgtccagccctgtg<br>accaagtccttcaaccggggcgagtgc |
| DNA coding sequence for:<br>$V_{L1}$-$L_1$-$V_{L2}$-$C_L$<br>(SEQ ID NO: 6)<br>With signal sequence | atgggctggtcctgcatcatcctgtttctggtggccacagccaccggc<br>gtgcacagcgaaatcgtgctgacccagagccccgccaccatgtctgcc<br>agccctggcgagagagtcaecatcacctgtagcgcccacagcagcgtc<br>agtttcatgcactggttccagcagaagcccggcaccagcccaaagct<br>tggatctacagcaccagcagcctcgccagcggcgtcccagctcgcttt<br>ggcggcagcggctctggcaccagctacagcctgaccatcagcagcatg<br>gaagccgaggacgccgccacctactactgccagcagcggagcagcttt<br>cccctgaccttcggcgctggcaccaagctggaactgaagggcggaggc<br>ggatccggcggcggaggctccgagattgtgctgacacagtctccagcc |

TABLE 2-continued

Polypeptide and DNA sequences for DS6 based B-Fab

|  |  |
|---|---|
|  | accatgagcgcctcccaggcgagcgcgtgacaatcacatgctccgcc<br>cactcctccgtgtcttttatgcattggtttcagcagaaacctgggaca<br>tcccctaaactctggatctactccacctcctccctggcctccggggtg<br>cccgctagatttggaggctctggcagcggcacctcctactccctgacc<br>atctcctctatggaagctgaagatgctgcaacatattattgccagcag<br>agaagctccttcccactgacatttggggccggaacaaagctcgagctg<br>aagcgtacggtggccgctccttccgtgttcatcttccctccctccgac<br>gagcagctgaagtccggcaccgcctccgtggtgtgtctgctgaacaac<br>ttctaccctcgggaggccaaggtgcagtggaaggtggacaacgccctg<br>cagtccggcaactcccaggagtccgtcaccgagcaggactccaaggac<br>agcacctactcctgtcctccaccctgaccctgtccaaggccgactac<br>gagaagcacaaggtgtacgcctgtgaggtgacccaccagggcctgtcc<br>agccctgtgaccaagtccttcaaccggggcgagtgc |
| Amino acid sequence for:<br>$V_{H1}-L_2-V_{H2}-C_{H1}$<br>(SEQ ID NO: 7) | EAQLVQSGAEVVKPGASVKMSCKASGYTFTSYNMHWVKQTPGQGLEWI<br>GYIYPGNGATNYNQKFQGKATLTADPSSSTAYMQISSLTSEDSAVYFC<br>ARGDSVPFAYWGQGTLVTVSA*GGGGSGGGGS*EAQLVQSGAEWKPGAS<br>VKMSCKASGYTFTSYNMHWVKQTPGQGLEWIGYIYPGNGATNYNQKFQ<br>GKATLTADPSSSTAYMQISSLTSEDSAVYFCARGDSVPFAYWGQGTLV<br>TVSAASTKGPSVFPLAPSSKSTSGGTAALGCLVKDYFPEPVTVSWNSG<br>ALTSGVHTFPAVLQSSGLYSLSSVVTVPSSSLGTQTYICNVNHKPSNT<br>KVDKKVEPKSCDKTHT |
| Amino acid sequence for:<br>Anti-CA6 $V_{H1}$<br>(SEQ ID NO: 8) | EAQLVQSGAEVVKPGASVKMSCKASGYTFTSYNMHWVKQTPGQGLEWI<br>GYIYPGNGATNYNQKFQGKATLTADPSSSTAYMQISSLTSEDSAVYFC<br>ARGDSVPFAYWGQGTLVTVSA |
| Amino acid sequence for:<br>$L_2$ Linker<br>(SEQ ID NO: 3) | GGGGSGGGGS |
| Amino acid sequence for:<br>Anti-CA6 $V_{H2}$<br>(SEQ ID NO: 8) | EAQLVQSGAEVVKPGASVKMSCKASGYTFTSYNMHWVKQTPGQGLEWI<br>GYIYPGNGATNYNQKFQGKATLTADPSSSTAYMQISSLTSEDSAVYFC<br>ARGDSVPFAYWGQGTLVTVSA |
| Amino acid sequence for:<br>$C_{H1}$ Human constant heavy<br>(SEQ ID NO: 9) | ASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDK<br>KVEPKSCDKTHT |
| DNA coding sequence for<br>$V_{H1}-L_2-V_{H2}-C_{H1}$<br>(SEQ ID NO: 10) | gaggcccagctggtgcagtctggcgctgaggtggtcaagcctggggcc<br>agcgtgaagatgagctgcaaggccagcggctacaccttcaccagctac<br>aacatgcactgggtcaagcagaccccagggcagggcctgaatggatt<br>ggctacatctaccccggcaacggcgccaccaactacaaccagaagttc<br>cagggcaaggctaccctgaccgccgaccctagcagcagcaccgcctac<br>atgcagatcagcagcctgaccagcgaggacagcgccgtgtacttctgc<br>gccagaggcgacagcgtgcccttcgcctattggggccagggcaccctg<br>gtcacagtgtctgctggtggcggaggatccggcggaggcggaagcgaa<br>gcccagctcgtccagagcggagccgaggtcgtgaaaccaggcgcctct<br>gtgaagatgtcttgcaaggcctctggctataccttttacctcctataat<br>atgcattgggtcaaacagacacctggacagggactcgagtggatcgga<br>tatatctatcctggaaatggggccacaaattacaatcagaaatttcag<br>gggaaagccacactgacagccgatcccagctcctccacagcctatatg<br>cagattagctctctgacctccgaggactccgccgtgtattttttgtgcc<br>cggggagactccgtgcctttttgcttactggggacagggcacactcgtg<br>acagtgtccgccgcttccaccaagggccctccgtgtttcctctggcc<br>cccagcagcaagagcacctctggcggaacagccgccctgggctgcctg<br>gtcaaggactacttccccgagcccgtgaccgtgtcttggaactctggc<br>gccctgacctccggcgtccacacctttccagccgtgctgcagagcagc<br>ggcctgtactctctgagcagcgtcgtgaccgtgcccagcagcagcctg<br>gggacccagacctacatctgcaacgtgaaccacaagcccagcaacacc<br>aaggtggacaagaaggtggaacccaagagctgcgacaagacccacacc |
| DNA coding sequence for<br>$V_{H1}-L_2-V_{H2}-C_{H1}$<br>(SEQ ID NO: 11)<br>With signal sequence. | atgggctggtcctgcatcatcctgtttctggtggccacagccaccggc<br>gtgcactctgaggcccagctggtgcagtctggcgctgaggtggtcaag<br>cctggggccagcgtgaagatgagctgcaaggccagcggctacaccttc<br>accagctacaacatgcactgggtcaagcagaccccagggcagggcctg<br>aatggattggctacatctaccccggcaacggcgccaccaactacaac<br>cagaagttccagggcaaggctaccctgaccgccgaccctagcagcagc<br>accgcctacatgcagatcagcagcctgaccagcgaggacagcgccgtg<br>tacttctgcgccagaggcgacagcgtgcccttcgcctattggggccag<br>ggcaccctggtcacagtgtctgctggtggcggaggatccggcggaggc<br>ggaagcgaagcccagctcgtccagagcggagccgaggtcgtgaaacca<br>ggcgcctctgtgaagatgtcttgcaaggcctctggctataccttttacc<br>tcctataatatgcattgggtcaaacagacacctggacagggactcgag<br>tggatcggatatatctatcctggaaatggggccacaaattacaatcag<br>aaatttcaggggaaagccacactgacagccgatcccagctcctccaca<br>gcctatatgcagattagctctctgacctccgaggactccgccgtgtat<br>ttttgtgcccggggagactccgtgcctttttgcttactggggacagggc |

TABLE 2-continued

Polypeptide and DNA sequences for DS6 based B-Fab

```
acactcgtgacagtgtccgccgcttccaccaagggccctccgtgttt
cctctggccccagcagcaagagcacctctggcggaacagccgcctg
ggctgcctggtcaaggactacttccccgagcccgtgaccgtgtcttgg
aactctggcgccctgacctccggcgtccacacctttccagccgtgctg
cagagcagcggcctgtactctctgagcagcgtcgtgaccgtgcccagc
agcagcctggggacccagacctacatctgcaacgtgaaccacaagccc
agcaacaccaaggtggacaagaaggtggaacccaagagctgcgacaag
acccacacc
```

Example 3: Development of Engineered Antibody-Like Binding Proteins Based on the DS6 Antibody In order to develop an imaging based companion diagnostic antibody-like binding protein for huDS6-DM4, three engineered antibody-like binding proteins (B-Fab, see FIG. 1) based on CA6 binding sequences from the humanized DS6 monoclonal antibody were created. Each of the three engineered antibody-like binding proteins was purified and tested as described below; the results are shown in Table 3. Desirable characteristics include >95% purity by HPLC or SDS-PAGE, ~10 mg/mL concentration, a stable peptide, binding similar to the DS6 antibody, and to determine whether the presence of a poly-histidine (6x-His) tag affects PET tracers. Additional selection criteria includes: a tumor signal of >5% ID/g; a tumor to muscle ratio of 3:1; efficient renal clearance; and a statistically significant difference ($p<0.05$) between unblocked and blocked uptake (see Table 4 for summary of quality criteria for radiolabeled chelated B-Fab).

TABLE 3

Summary of DS6 engineered antibody-like binding proteins

| Format | Description | Purity ID (SEC) (MS) | Stability (Tmelt) | $K_d$ (nM) |
| --- | --- | --- | --- | --- |
| B-Fab 1151 | (G4S)$_2$ linker with C-terminal 6xHis tag | >95% OK | 58° C. | 3.4 |
| B-Fab 1152 | G4S linker with C-terminal 6xHis tag | >95% OK | 59° C. | 88 |
| B-Fab 1153 | (G4S)$_2$ linker without C-terminal 6xHis tag | >95% OK | 57° C. | 2.3 |
| DS6 mAb | Control DS6 monoclonal antibody | | | 2.0 |

TABLE 4

Summary of quality criteria for radiolabeled chelated antibody-like binding protein

| Imaging Companion Diagnostic Test Specifications | Acceptance Criteria/Limit |
| --- | --- |
| Purity (HPLC) | >95-98% monomeric |
| In vitro cell binding assay | >90% for CA6+ cell lines |
| | <5% for CA6− cell lines - low nM |
| Stability | >80% after 24 hours at 37° C. in serum |
| Imaging parameters | Tumor % IC/g ≥5 |
| | Tumor to normal tissue ratio 3:1 |
| | Specific Activity (Ci/μmole) 2-5 |

It was determined that the B-Fab antibody containing a (G45)$_2$ linker, and with or without a 6x-His tag, maintained binding efficiencies similar to the control DS6 monoclonal antibody from which the CA6 binding sequences were based. The quality of each of the purified antibody-like binding protein was checked by the following analytical methods:

a) Analytical Size-Exclusion Chromatography (SEC)

Analytical SEC was performed using an ÄKTA explorer 10 (GE Healthcare) equipped with a TSKgel G3000SWXL column (7.8 mm×30 cm) and TSKgel SWXL guard column (Tosoh Bioscience). The analysis was run at 1 mL/min using 250 mM NaCl, 100 mM Na-phosphate pH 6.7 with detection at 280 nm. Thirty microliters of protein sample (at 0.5-1 mg/mL) were applied onto the column. For estimation of the molecular size, the column is calibrated using a gel filtration standard mixture (MWGF-1000, SIGMA Aldrich). Data evaluation was performed using UNICORN software v5.11.

b) Intact Mass Analysis by LC-MS

Each sample was diluted to a concentration of 0.01 mg/mL and then reduced by adding DTT (final 10 mM). Prior to separation, the sample was trapped for 20 minutes and desalted with 20 μL/min on a monolithic trap column with 2% Acetonitrile/0.1% TFA (v/v) prior to elution with a gradient ranging from 15% Eluent A (H$_2$O/0.05% TFA) to 50% Eluent B (Acetonitrile/0.05% TFA).

Each sample was separated operating in nanoflow (300 mL/min) on a monolithic column (PSDVB; 100 μm I.D.×5 cm) at 37° C. Introduction of each sample was carried out using electrospray needles from new objective with an outer diameter of 365 μm, inner diameter of 75 μm and an end tip diameter of 15 μm plus sheath gas. After acquisition on a QStar XL, the spectra were summed over the corresponding time range and deconvoluted using the protein reconstruction tool delivered with BioAnalyst from Applied Biosystems/MDS Sciex.

c) Protein Identification by Peptide Mass Fingerprint Analysis Using LC-MS

The lane of interest was punched out, carbamidomethylated and digested with endoproteinase trypsin. Subsequently the sample was analyzed by LC-MS/MS using an OrbiTrap XL mass spectrometer. The obtained spectra were compared with the user defined database Swiss-Prot PP to which the given construct was added, as well as to the database Swiss-Prot all species.

Figure 2A:
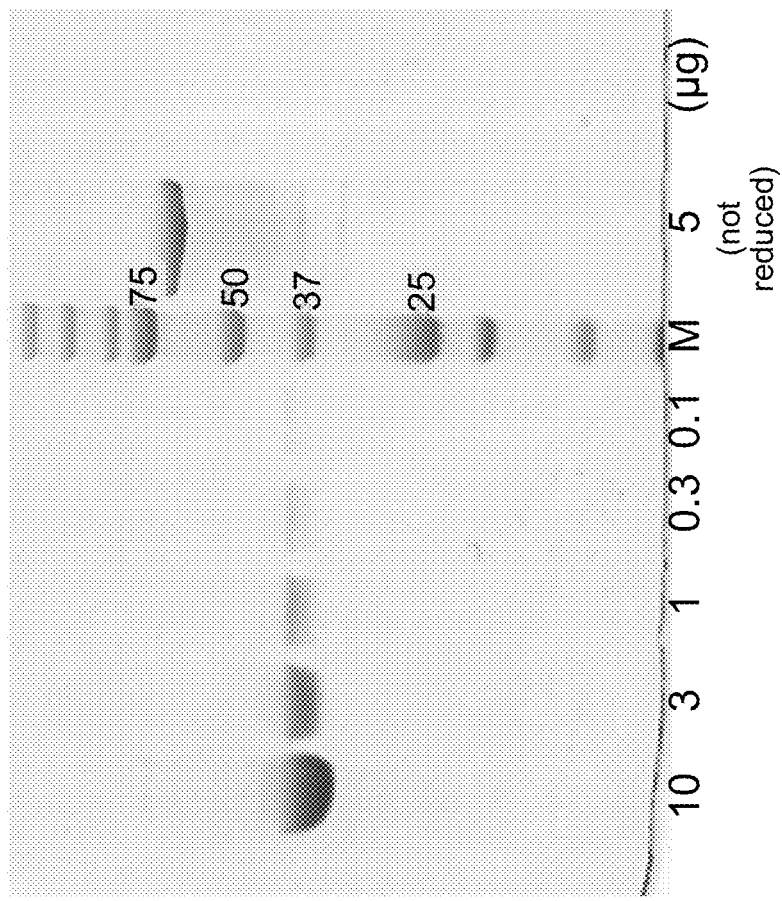
FIG. 2. Assessment of the B-Fab DS6 based engineered antibody with GGGGSGGGGS ((G45)₂) linker (SEQ ID NO: 3) and C-terminal 6x-His tag via gel electrophoresis (FIG. 2A), size-exclusion chromatography (SEC) (FIG. 2B), and Fluorescence Activated Cell Sorting (FACS) (FIG. 2C and FIG. 2D).
Figure 2B:
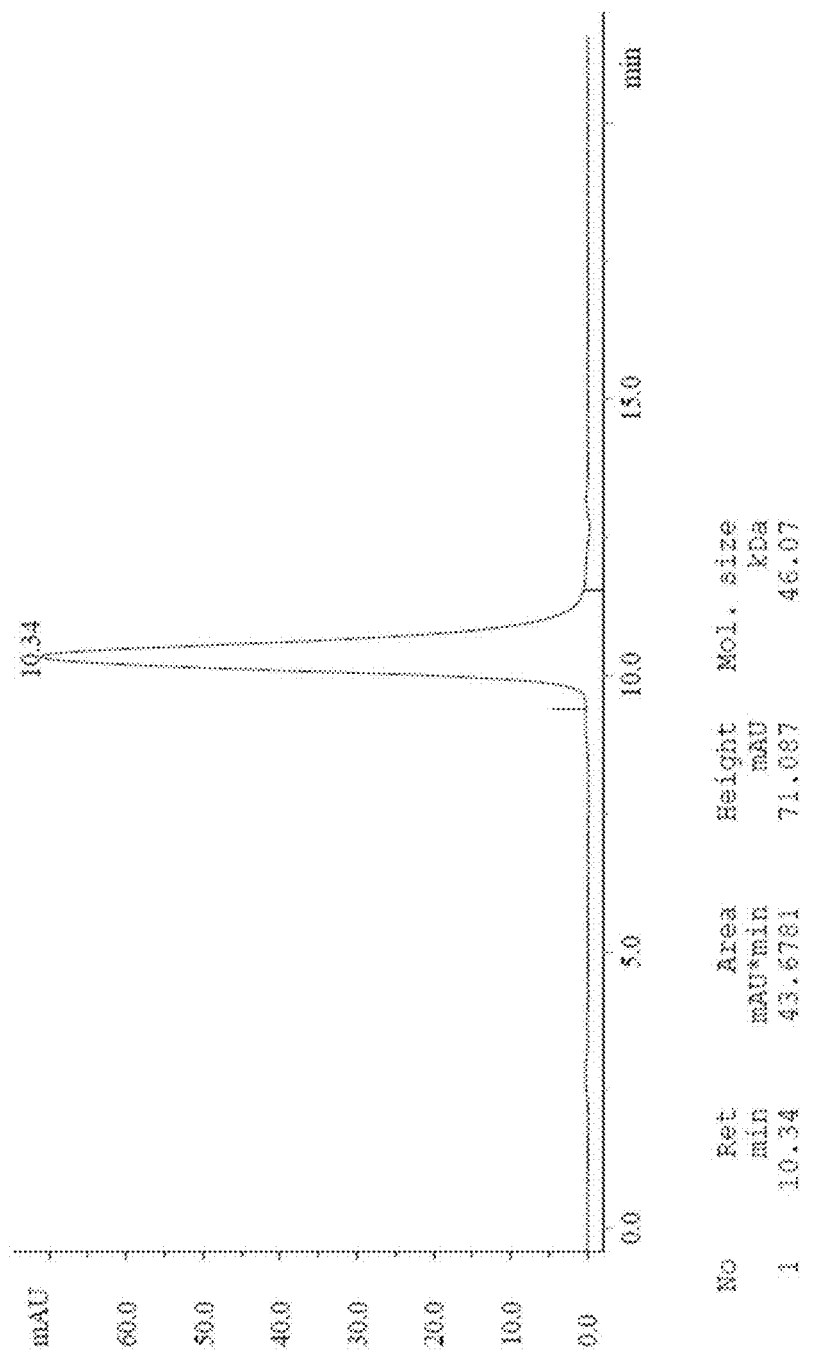

Each of three engineered DS6-based antibody-like binding proteins were chemically conjugated to the hard acid cation chelator DOTA (1,4,7,10-tetraazacyclododecane-1,4,7,10-tetraacetic acid), radiolabeled with $^{64}$Cu, and used for in vivo PET bio-imaging experiments in preclinical tumor models and in vitro cell binding assays in order to characterize each of the three engineered DS6-based antibody-like binding proteins. A summary of the data from the activities and experiments for each engineered antibody can be seen in Table 5 and FIGS. 2-4.

TABLE 5

Summary of activities of DS6 engineered antibody-like binding proteins

|  | B-Fabs |
|---|---|
| Purity (SEC) | >95% |
| In vitro stability: | |
| Freeze/thaw stress (3x −80° C./RT) | Well tolerated |
| Heat stress (1 week at 42° C.) | Well tolerated |
| Serum stability (24 hours at 37° C.) | >90% monomeric |
| FACS binding affinities (WISH cell line, CA6+) | 2 nM |
| Radiochemistry yield | 60-80% |
| Imaging parameters: | |
| Tumor (WISH, CA6+) | 7.5-10.4% ID/g |
| Tumor (A2780, CA6−) | 4-5.6% ID/g |
| Biodistribution | |
| Liver | 7-10% ID/g |
| Kidney | 57-73% ID/g |
| Blood | 2-3% ID/g |
| Muscle | ~1% ID/g |
| WISH tumor to normal tissue ratio: | |
| Tumor/Blood | 4-6 |
| Tumor/Muscle | 9-11 |
| WISH (CA6+) tumor to A2780 (CA6−) tumor ratio | 1.7-1.9 |

WISH is a cell line positive for the CA6 antigen.
A2780 is a cell line negative for the CA6 antigen.

All the above antibody-like binding proteins and their corresponding DOTA conjugates (1.5-2.5 DOTA/fragment) had high affinity ($K_D$=4-20 nM) to CA6 positive cells (WISH cell line), indicating that DOTA derivatization does not adversely affect the affinity towards the antigen. The fragments had low affinity towards CA6 negative cells (A2780 cell line). The $^{64}$Cu labeled agents were evaluated by human serum stability studies and in vivo imaging and 24-hour biodistribution studies in nude mice bearing either WISH or A2780 subcutaneous tumors. The $^{64}$Cu-DOTA-B-Fab was synthesized in high yield (RCY—80%, SA—55 GBq/μmole, >99% purity) and gave good results in 24 hour serum stability (94±5%, n=3) tests. In-vivo biodistribution experiments (see Table 6) in xenograft tumor-bearing mice showed relatively high WISH tumor uptake (7.6±0.87% ID/g, n=4, 20-206 mg) and low A2780 tumor uptake (5.1±0.92% ID/g, n=3, 50-270 mg) combined with high tumor/muscle (8.7:1), tumor/blood (3.6:1) and positive/negative tumor (1.8, p<0.05, n=7) ratios. Tumor uptake was surpassed only by the kidneys (62±4% ID/g) and liver (10±0.75% ID/g).

TABLE 6

Summary of biodistribution studies in xenograft tumor bearing mice

| | WISH tumor (% ID/g) | A2780 tumor (% ID/g) | WISH/A2780 ratio | Liver (% ID/g) | Kidneys (% ID/g) |
|---|---|---|---|---|---|
| $^{64}$Cu-DOTA-B-Fab | 7.6 ± 0.87 | 5.1 ± 0.92 | 1.5 | 10 ± 0.75 | 62 ± 4 |
| $^{64}$Cu-DOTA-anti lyzosyme-B-Fab | 4.84 ± 1.02 | 3.84 ± 0.49 | 1.26 | 15.2 ± 1.3 | 70 ± 9.6 |
| $^{64}$Cu-DOTA-anti-DM4-B-Fab | 4.04 ± 0.43 | 3.03 ± 0.24 | 1.33 | 10.4 ± 1.6 | 52 ± 8.3 |

$^{64}$Cu-DOTA-B-Fab was further evaluated in WISH bearing tumor animals for specificity via blocking studies in vivo. Blocking was performed either by administration of B-Fab (2 mg, n = 5) or DS6 (1 mg, n = 4) at 2.5 or 25 hours respectively prior to the administration of the radiolabeled agent. B-Fab blocking afforded a 23% (p<0.05, n = 8) decrease in WISH tumor uptake while DS6 blocking achieved a 26% (p<0.05, n = 7) decrease. Control tumors (n = 3) were not blocked in this study. These preclinical studies suggest that $^{64}$Cu-DOTA-B-Fab is a suitable companion diagnostic for huDS6-DM4 in patients.

Figures 2C, 2D:
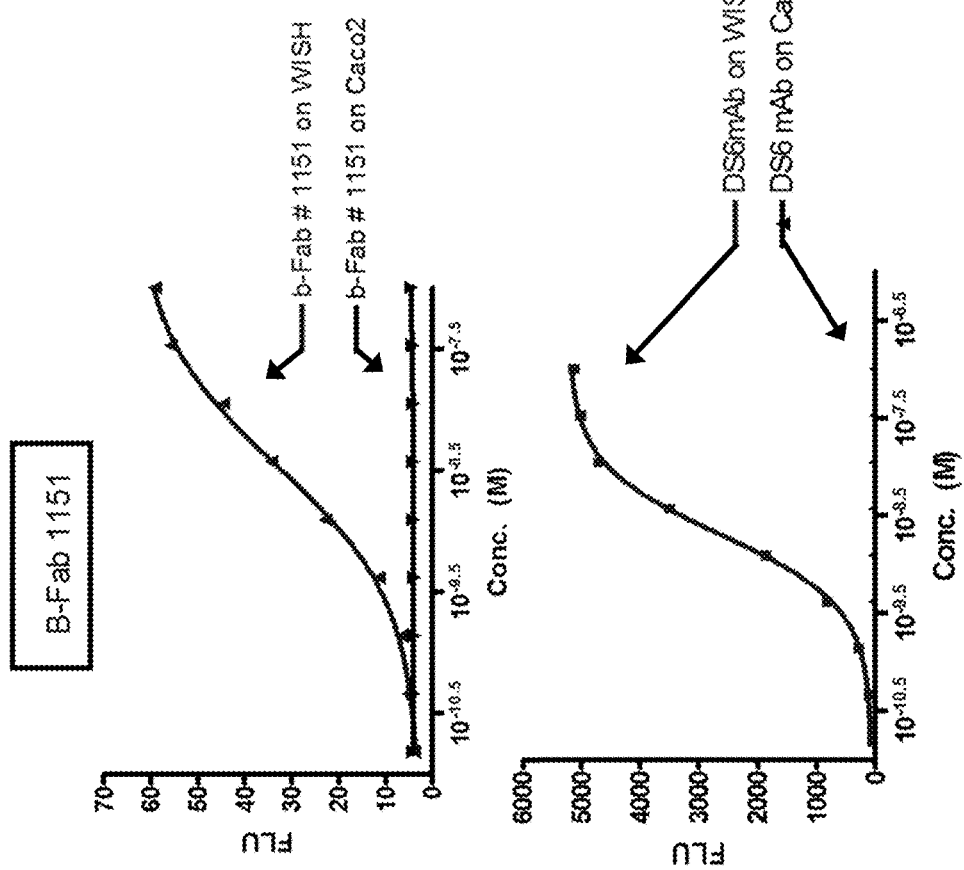

Example 4: In Vivo PET Studies of Developed Engineered Antibodies in Preclinical Tumor Models a) B-Fab (G4S)$_2$ Linker and C-Terminal 6x-his Tag The B-Fab 1151 is a DS6-based engineered antibody like binding protein containing both L1 and L2 linkers as GGGGSGGGGS ((G4S)$_2$) (SEQ ID NO: 3) and containing a C-terminal 6x-His tag expressed. The protein was purified by IMAC and SEC and in vitro binding solution was prepared at 1.8 mg/ml in PBS and binding affinity was characterized using flow cytometry in the WISH CA6+ cell line (FIG. 2C and FIG. 2D).

b) B-Fab (G4S)$_2$ Linker

Figure 3A:
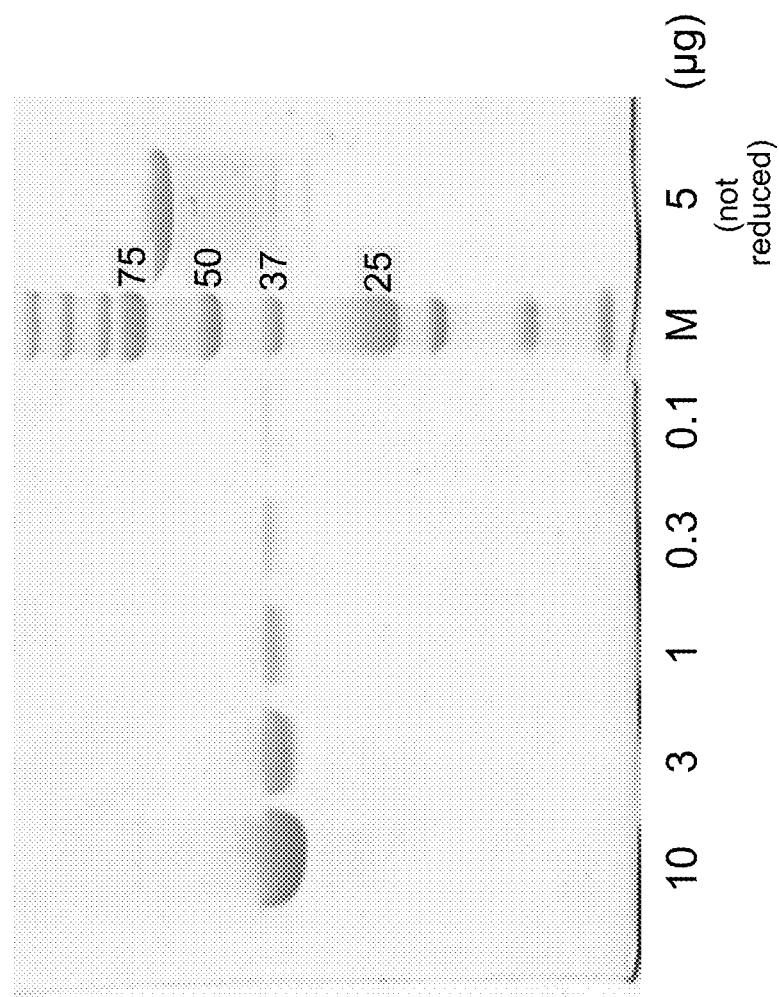
FIG. 3. Assessment of the B-Fab DS6 based engineered antibody with (G45)₂ linker via gel electrophoresis (FIG. 3A), SEC (FIG. 3B), and FACS (FIG. 3C and FIG. 3D).
Figure 3B:
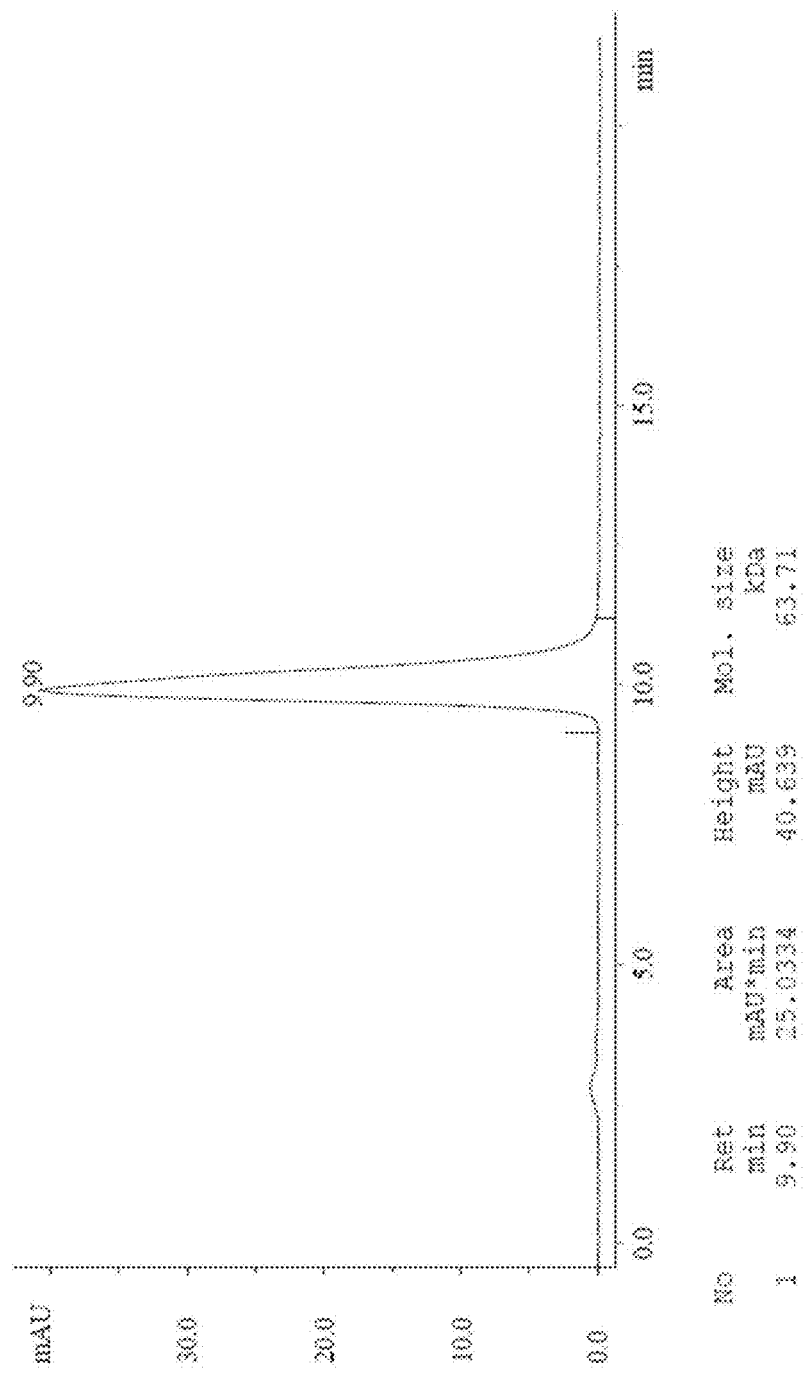
Figure 3C:
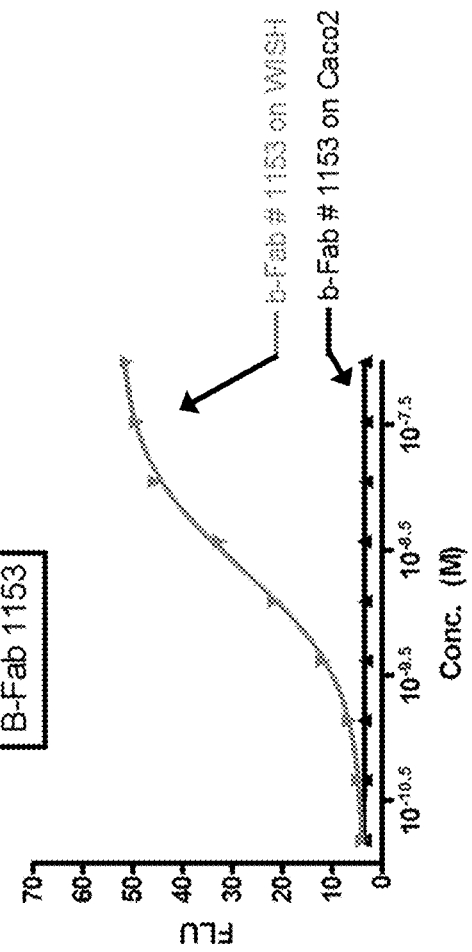
Figure 3D:
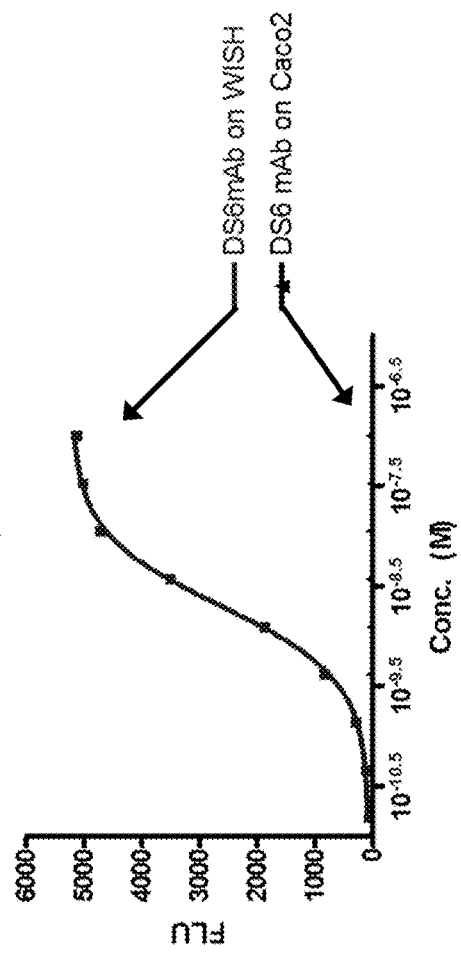
Figure 4B:
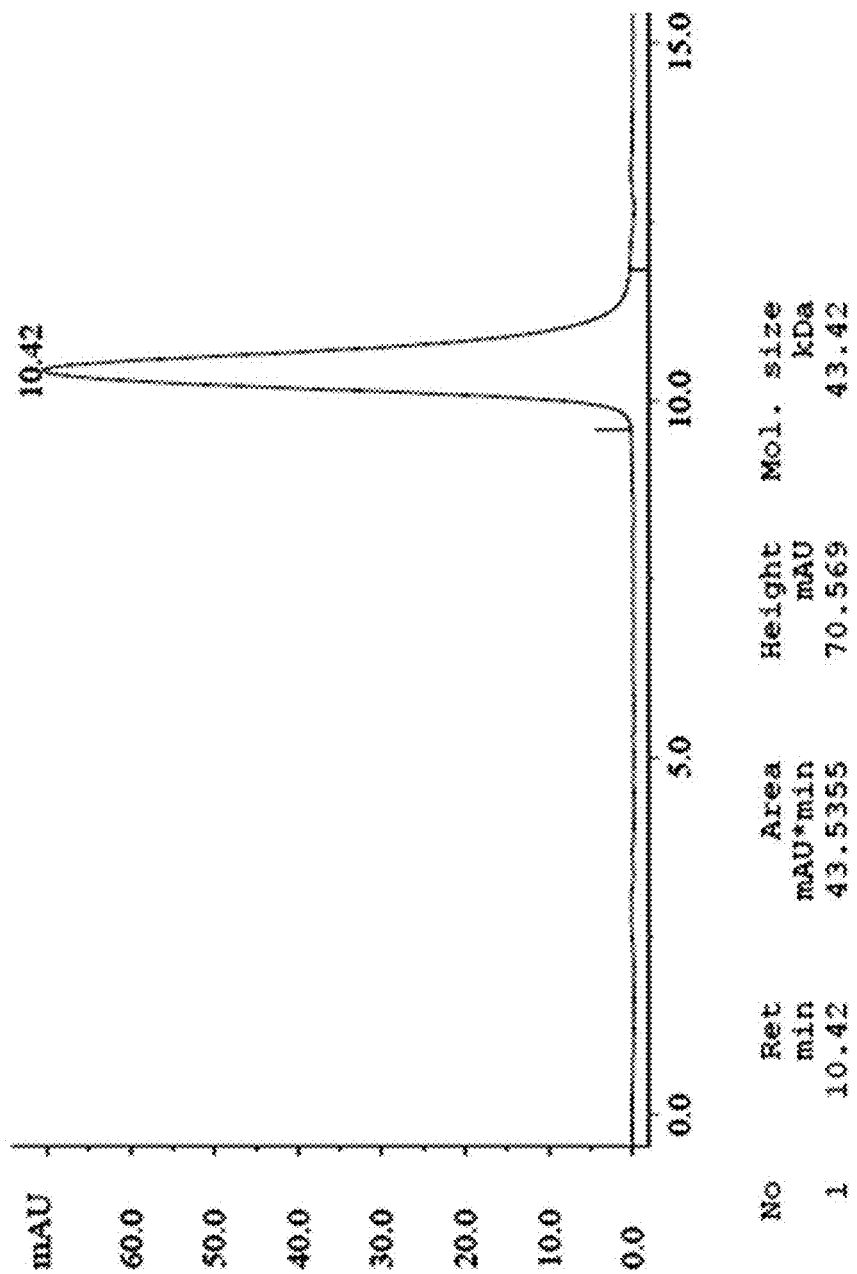
FIG. 4. Assessment of the B-Fab DS6 based engineered antibody with GGGGS (G4S) linker and C-terminal 6x-His tag via gel electrophoresis (FIG. 4A), SEC (FIG. 4B), and FACS (FIG. 4C and FIG. 4D).

The B-Fab 1153 is a DS6-based engineered antibody-like binding protein containing a both L1 and L2 linkers as (G4S)$_2$ and not containing a C-terminal 6x-His tag. Since this protein was lacking a His tag the protein was purified by IMAC, Kappa-select and SEC. The in vitro binding solution was prepared at 1.6 mg/ml in PBS and binding affinity was characterized using flow cytometry in the WISH CA6+ cell line (FIG. 3C and FIG. 3D).

c) B-Fab G4S Linker and C-Terminal 6x-his Tag

Figure 4C:
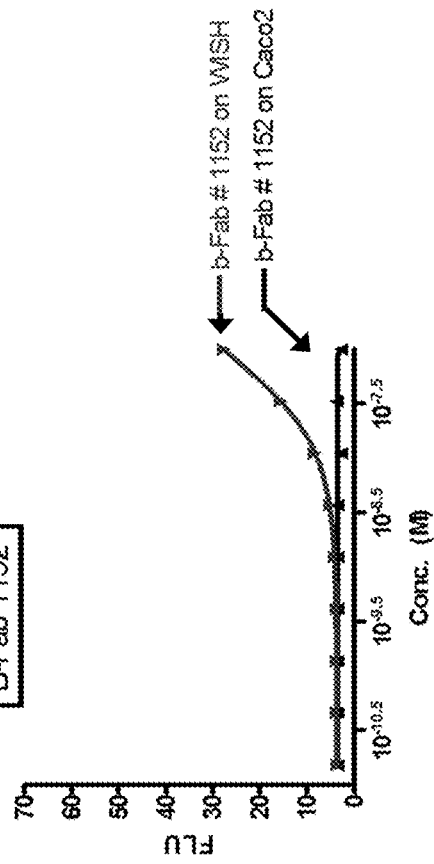
Figure 4D:
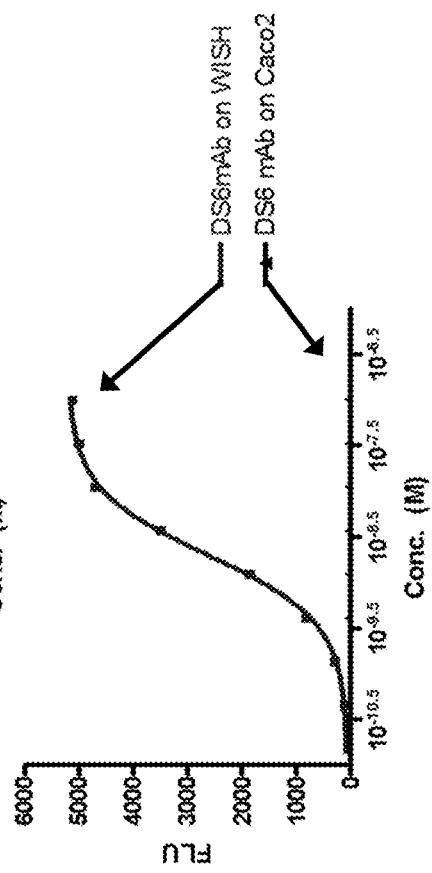

The B-Fab 1152 is a DS6-based engineered antibody-like binding protein containing a both L1 and L2 linkers as a single copy of G4S and containing a C-terminal 6x-His tag. The protein was purified by IMAC and SEC and the in vitro binding solution was prepared at 1.8 mg/ml in PBS and binding affinity was characterized using flow cytometry in the WISH CA6+ cell line (FIG. 4C and FIG. 4D).

Example 5: In Vitro Binding Results for DS6 with and without DOTA

Figures 5A, 5B, 5C:
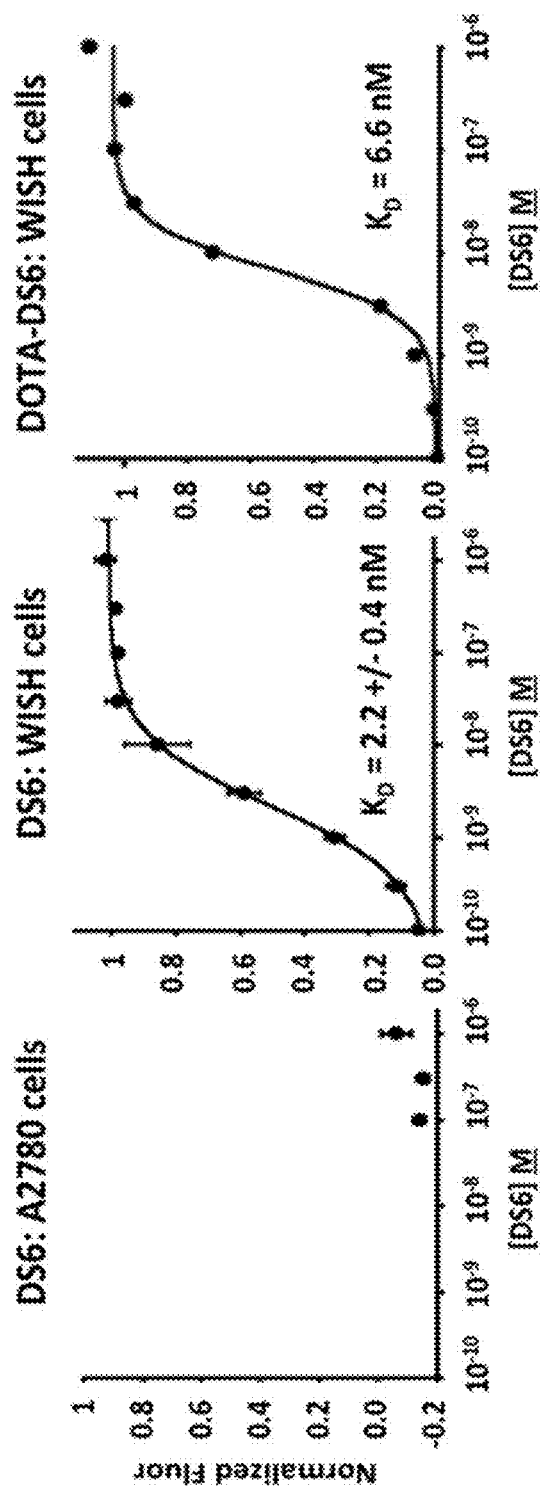
FIG. 5. Assessment of the B-Fab DS6 based engineered antibody via FACS using A2780 cells without DOTA (FIG. 5A), WISH cells without DOTA (FIG. 5B), and WISH cells with DOTA (FIG. 5C), demonstrates that DOTA conjugation does not alter DS6 binding.

In order to show that DOTA conjugation does not alter DS6 activity, binding of the DS6 antibody-like binding protein and the DOTA-DS6 conjugated antibody was tested in vitro on CA6 positive WISH cell line and the A2780 CA6 negative cell line. Fluorescent activated cell sorting experiments determined that DOTA conjugation does not alter DS6 binding in the CA6 positive WISH cells (see FIG. 5).

Figure 6A:
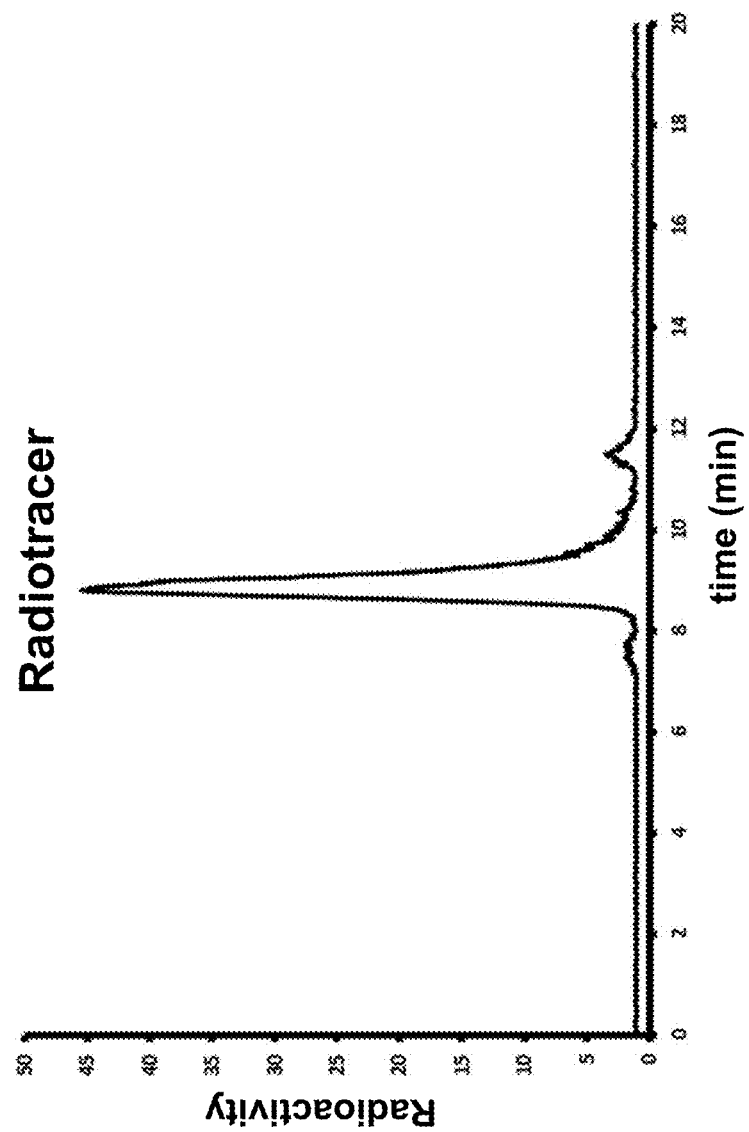
FIG. 6. Assessment of the $^{64}$Cu-DOTA-DS6 B-Fab antibody-like binding protein demonstrates that radiolabelling with $^{64}$Cu and DOTA conjugation allows for ideal radiochemistry (FIG. 6A) and serum stability (FIG. 6B).

Example 6: Radiolabeling and Stability of $^{64}$Cu-DOTA-DS6 B-Fab Antibody-Like Binding Protein Human serum stability studies and 24-hour biodistribution studies using DOTA conjugated DS6 B-Fab labeled with copper-64 were performed in nude mice bearing either CA6 positive (WISH) or CA6 negative (A2780) subcutaneous tumors were. Radiochemistry studies show that the $^{64}$Cu-DOTA-DS6 B-Fab engineered antibody-like binding protein has a radiochemical yield of ~30%, a radiochemical purity of >95%, and a specific activity of 1.9 Ci/µmole (see FIG. 6A). Serum stability experiments of the $^{64}$Cu-DOTA-DS6 B-Fab antibody-like binding protein were performed for 24 hours in human serum at 37° C., and show 97.2% activity at the 0 hour time point and 96.3% activity at the 24 hour time point, demonstrating no significant loss in activity after 24 hours (see FIG. 6B).

Example 7: Comparison Between Antibody-Like Binding Proteins Having Different Scaffolds The properties of the B-Fab antibody-like binding protein described above were compared with those of a diabody that specifically binds CA6, in order to assess which scaffold would be the most suitable for use as an imaging companion diagnostic. The amino acid sequence of that anti-CA6 diabody, which forms a homodimer, is shown as SEQ ID NO: 12 (Table 7). In some experiments, that homodimeric diabody further comprised a C-terminal tag selected from the group consisting of a GGC tag, a tag of SEQ ID NO: 13, and a tag of SEQ ID NO: 14.

Figures 7A, 7B:
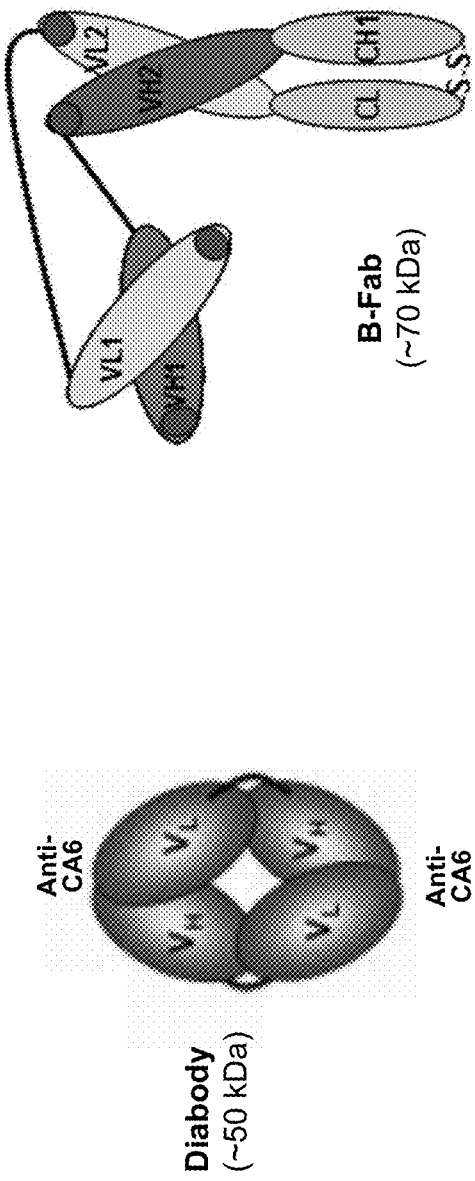
FIG. 7. Comparison between antibody-like binding proteins having a diabody scaffold (FIG. 7A) and B-Fab scaffold (FIG. 7B).

As shown in FIG. 7, the diabody has a scaffold that is different from the scaffold of the B-Fab antibody-like binding protein. For instance, it does not comprise any $C_L$ or any $C_{H1}$ domain.

TABLE 7

| Polypeptide sequence for the diabody that specifically binds CA6 | |
|---|---|
| Amino acid sequence for the diabody (SEQ ID NO: 12) | EIVLTQSPATMSASPGERVTITCSAHSSVSFMHWFQQKPGTSPKLWIY STSSLASGVPARFGGSGSGTSYSLTISSMEAEDAATYYCQQRSSFPLT FGAGTKLELKGGGSGGGGEAQLVQSGAEVVKPGASVKMSCKASGYTFT SYNMHWVKQTPGQGLEWIGYIYPGNGATNYNQKFQGKATLTADPSSST AYMQISSLTSEDSAVYFCARGDSVPFAYWGQGTLVTVSA |
| C-terminal tag (SEQ ID NO: 13) | GGHHHHHH |
| C-terminal tag (SEQ ID NO: 14) | GGCGGHHHHHH |

The results are shown in tables 8A to 8C below. These results were obtained by comparing a diabody of SEQ ID NO: 12 fused to a tag of SEQ ID NO: 14, with the B-Fab 1153 (which contains a (G4S)2 linker but no His-tag).

TABLE 8A

Comparison between the B-Fab and the diabody

| Scaffold | Aggregation (SEC) | In Vitro Stability: Freeze/thaw stress (3X −80° C.-->RT) | In Vitro Stability: Heat Stress (1 week at 42° C.) | FACS binding assay (Free) Kd app (nM) | FACS binding assay (DATA Conjugate) Kd app (nM) |
|---|---|---|---|---|---|
| B-Fab | >95% monomeric | Well tolerated | Well tolerated | 4 | 7.4 |
| Diabody | >95% monomeric | Well tolerated | Significant loss (~25%) of soluble protein | 10 | 7.5 |

TABLE 8B

Comparison between the B-Fab and the diabody

| Scaffold | Radio chemical yield | Radio chemical purity | Specific acitivity (Ci/µMole) | Serum stability of radiolabeled scaffolds: 24 h at 37° C. |
|---|---|---|---|---|
| B-Fab | 40-80% | >99% | 1.5 | >90% monomeric |
| Diabody | 10-15% | >99% | 0.3 | ~40% monomeric |

TABLE 8C

Comparison between the B-Fab and the diabody

| Scaffold | Tumor signal in antigen positive tumor model (WISH) (% ID/g) 24 hrs P.I. | Tumor signal in antigen negative tumor model (A2780) (% ID/g) 24 hrs P.I. | Tumor to muscle ratio in antigen positive tumor model (WISH) 24 hrs P.I. | Tumor to blood ratio in antigen positive tumor model (A2780) 24 hrs P.I. | Primary route of clearance | Biodistribution Profile 24 hrs Post Injection (P.I.) |
|---|---|---|---|---|---|---|
| B-Fab | 7.5-10.4 [Three independent expts] | 4-5.6 [Three independent expts] | 9-11 [Three independent expts] | 4-6 [Three independent expts] | Renal | Yes Kidney: 57-73% ID/g Liver: 7-10% ID/g |
| Diabody | 4.3 | 3.2 | ~4 | ~2 | Renal | Yes Kidney: 104% ID/g Liver: 10% IDg |

From these results it can be concluded that the B-Fab is better than the diabody for use as a companion diagnostic. For example, the diabody presented degradation in the plasma stability assay and in the temperature stress assay, whereas the B-Fab was stable in both assays.

While the invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

The invention claimed is:

1. An antibody-like binding protein that specifically binds CA6, wherein the antibody-like binding protein comprises two polypeptides having structures represented by the formulas [I] and [II] below:

$$V_{L1}\text{-}L_1\text{-}V_{L2}\text{-}C_L \quad [I]$$

$$V_{H1}\text{-}L_2\text{-}V_{H2}\text{-}C_{H1} \quad [II]$$

wherein:
- $V_{L1}$ is a DS6-based immunoglobulin light chain variable domain comprising SEQ ID NO: 2;
- $V_{L2}$ is a DS6-based immunoglobulin light chain variable domain comprising SEQ ID NO: 2;
- $V_{H1}$ is a DS6-based immunoglobulin heavy chain variable domain comprising SEQ ID NO: 8;
- $V_{H2}$ is a DS6-based immunoglobulin heavy chain variable domain comprising SEQ ID NO: 8;
- $C_L$ is an immunoglobulin light chain constant domain;
- $C_{H1}$ is an immunoglobulin $C_{H1}$ heavy chain constant domain;
- $L_1$ and $L_2$ are amino acid linkers;

wherein the polypeptides of formula I and the polypeptides of formula II form a bivalent monospecific tandem immunoglobulin antibody-like binding protein; and
wherein the antibody-like protein further comprises a chelator.

2. The antibody-like binding protein of claim 1, wherein the polypeptide of formula [I] comprises SEQ ID NO: 1.

3. The antibody-like binding protein of claim 1, wherein the polypeptide of formula [II] comprises SEQ ID NO: 7.

4. The antibody-like binding protein of claim 1, wherein the chelator is a hard acid cation chelator.

5. The antibody-like binding protein of claim 4, wherein the hard acid cation chelator is DOTA (1,4,7,10-tetraazacyclododecane-1,4,7,10-tetraacetic acid), NOTA (1,4,7-triazacyclononane-N,N',N''-triacetic acid), DTPA (1,1,4,7,7-Diethylenetriaminepentaacetic acid), or TETA (p-bromoacetamido-benzyl-tetraethylaminetetraacetic acid).

6. The antibody-like binding protein of claim 5, wherein the hard acid cation chelator is DOTA.

7. The antibody-like binding protein of claim 1, further comprising at least one radiolabel, imaging agent, therapeutic agent, or diagnostic agent.

8. The antibody-like binding protein of claim 7, wherein the radiolabel, imaging agent, therapeutic agent, or diagnostic agent is $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, or $^{83}$Sr.

9. The antibody-like binding protein of claim 8, wherein the radiolabel, imaging agent, therapeutic agent, or diagnostic agent is $^{64}$Cu.

10. A pharmaceutical composition comprising a pharmaceutically acceptable carrier and an amount of the antibody-like binding protein of claim 1 effective to image a CA6 expressing tissue.

11. The antibody-like binding protein of claim 1, wherein $C_L$ is a human IGKC immunoglobulin light chain constant domain.

12. The antibody-like binding protein of claim 1, wherein $C_{H1}$ is a human immunoglobulin $C_{H1}$ heavy chain constant domain.

* * * * *

```
                        SEQUENCE LISTING

<160> NUMBER OF SEQ ID NOS: 14

<210> SEQ ID NO 1
<211> LENGTH: 329
<212> TYPE: PRT
<213> ORGANISM: Artificial Sequence
<220> FEATURE:
<223> OTHER INFORMATION: Synthetic peptide

<400> SEQUENCE: 1

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
                20                  25                  30

His Trp Phe Gln Gln Lys Pro Gly Thr Ser Pro Lys Leu Trp Ile Tyr
            35                  40                  45

Ser Thr Ser Ser Leu Ala Ser Gly Val Pro Ala Arg Phe Gly Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Glu Ile Val Leu Thr Gln Ser Pro Ala Thr Met Ser
        115                 120                 125

Ala Ser Pro Gly Glu Arg Val Thr Ile Thr Cys Ser Ala His Ser Ser
    130                 135                 140
```

```
Val Ser Phe Met His Trp Phe Gln Gln Lys Pro Gly Thr Ser Pro Lys
145                 150                 155                 160

Leu Trp Ile Tyr Ser Thr Ser Leu Ala Ser Gly Val Pro Ala Arg
            165                 170                 175

Phe Gly Gly Ser Gly Ser Gly Thr Ser Tyr Ser Leu Thr Ile Ser Ser
            180                 185                 190

Met Glu Ala Glu Asp Ala Ala Thr Tyr Tyr Cys Gln Gln Arg Ser Ser
            195                 200                 205

Phe Pro Leu Thr Phe Gly Ala Gly Thr Lys Leu Glu Leu Lys Arg Thr
            210                 215                 220

Val Ala Ala Pro Ser Val Phe Ile Phe Pro Pro Ser Asp Glu Gln Leu
225                 230                 235                 240

Lys Ser Gly Thr Ala Ser Val Val Cys Leu Leu Asn Asn Phe Tyr Pro
            245                 250                 255

Arg Glu Ala Lys Val Gln Trp Lys Val Asp Asn Ala Leu Gln Ser Gly
            260                 265                 270

Asn Ser Gln Glu Ser Val Thr Glu Gln Asp Ser Lys Asp Ser Thr Tyr
            275                 280                 285

Ser Leu Ser Ser Thr Leu Thr Leu Ser Lys Ala Asp Tyr Glu Lys His
            290                 295                 300

Lys Val Tyr Ala Cys Glu Val Thr His Gln Gly Leu Ser Ser Pro Val
305                 310                 315                 320

Thr Lys Ser Phe Asn Arg Gly Glu Cys
            325

<210> SEQ ID NO 2
<211> LENGTH: 106
<212> TYPE: PRT
<213> ORGANISM: Artificial Sequence
<220> FEATURE:
<223> OTHER INFORMATION: Synthetic peptide

<400> SEQUENCE: 2

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
            35                  40                  45

Ser Thr Ser Ser Leu Ala Ser Gly Val Pro Ala Arg Phe Gly Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Gly Gly Gly Gly Ser Gly Gly Gly Gly Ser
```

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 987
<212> TYPE: DNA
<213> ORGANISM: Artificial Sequence
<220> FEATURE:
<223> OTHER INFORMATION: Synthetic oligonucleotide

<400> SEQUENCE: 5
gaaatcgtgc tgacccagag ccccgccacc atgtctgcca gccctggcga gagagtcacc      60
atcacctgta gcgcccacag cagcgtcagt ttcatgcact ggttccagca gaagcccggc     120
accagcccaa agctgtggat ctacagcacc agcagcctcg ccagcggcgt cccagctcgc     180
tttggcggca gcggctctgg caccagctac agcctgacca tcagcagcat ggaagccgag     240
gacgccgcca cctactactg ccagcagcgg agcagctttc ccctgacctt cggcgctggc     300
accaagctgg aactgaaggg cggaggcgga tccggcggcg gaggctccga gattgtgctg     360
acacagtctc cagccaccat gagcgcctcc caggcgagc gcgtgacaat cacatgctcc     420
gcccactcct ccgtgtcttt tatgcattgg tttcagcaga aacctgggac atcccctaaa     480
ctctggatct actccacctc ctccctggcc tccggggtgc ccgctagatt tggaggctct     540
ggcagcggca cctcctactc cctgaccatc tcctctatgg aagctgaaga tgctgcaaca     600
tattattgcc agcagagaag ctccttccca ctgacatttg ggccggaac aaaagctcgag     660
ctgaagcgta cggtggccgc tccttccgtg ttcatcttcc ctcccctccga cgagcagctg     720
aagtccggca ccgcctccgt ggtgtgtctg ctgaacaact tctaccctcg ggaggccaag     780
gtgcagtgga aggtggacaa cgccctgcag tccggcaact cccaggagtc cgtcaccgag     840
caggactcca aggacagcac ctactccctg tcctccaccc tgaccctgtc caaggccgac     900
tacgagaagc acaaggtgta cgcctgtgag gtgacccacc agggcctgtc cagccctgtg     960
accaagtcct tcaaccgggg cgagtgc                                         987

<210> SEQ ID NO 6
<211> LENGTH: 1044
<212> TYPE: DNA

<213> ORGANISM: Artificial Sequence
<220> FEATURE:
<223> OTHER INFORMATION: Synthetic oligonucleotide

<400> SEQUENCE: 6

```
atgggctggt cctgcatcat cctgtttctg gtggccacag ccaccggcgt gcacagcgaa      60
atcgtgctga cccagagccc cgccaccatg tctgccagcc tggcgagag agtcaccatc     120
acctgtagcg cccacagcag cgtcagtttc atgcactggt tccagcagaa gcccggcacc    180
agcccaaagc tgtggatcta cagcaccagc agcctcgcca gcggcgtccc agctcgcttt    240
ggcggcagcg gctctggcac cagctacagc ctgaccatca gcagcatgga agccgaggac    300
gccgccacct actactgcca gcagcggagc agctttcccc tgaccttcgg cgctggcacc    360
aagctggaac tgaagggcgg aggcggatcc ggcggcggag gctccgagat tgtgctgaca    420
cagtctccag ccaccatgag cgcctcccca ggcgagcgcg tgacaatcac atgctccgcc    480
cactcctccg tgtctttat gcattggttt cagcagaaac ctgggacatc ccctaaactc    540
tggatctact ccacctcctc cctggcctcc ggggtgcccg ctagatttgg aggctctggc    600
agcggcacct cctactccct gaccatctcc tctatggaag ctgaagatgc tgcaacatat    660
tattgccagc agagaagctc cttcccactg acatttgggg ccggaacaaa gctcgagctg    720
aagcgtacgg tggccgctcc ttccgtgttc atcttccctc cctccgacga gcagctgaag    780
tccggcaccg cctccgtggt gtgtctgctg aacaacttct accctcggga ggccaaggtg    840
cagtggaagg tggacaacgc cctgcagtcc ggcaactccc aggagtccgt caccgagcag    900
gactccaagg acagcaccta ctccctgtcc tccaccctga ccctgtccaa ggccgactac    960
gagaagcaca aggtgtacgc ctgtgaggtg acccaccagg gcctgtccag ccctgtgacc   1020
aagtccttca ccggggcga gtgc                                          1044
```

<210> SEQ ID NO 7
<211> LENGTH: 352
<212> TYPE: PRT
<213> ORGANISM: Artificial Sequence
<220> FEATURE:
<223> OTHER INFORMATION: Synthetic peptide

<400> SEQUENCE: 7

```
Glu Ala Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Ala Thr Asn Tyr Asn Gln Lys Phe
    50                  55                  60

Gln Gly Lys Ala Thr Leu Thr Ala Asp Pro Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala Gly Gly Gly Ser Gly Gly Gly Gly Ser Glu
        115                 120                 125

Ala Gln Leu Val Gln Ser Gly Ala Glu Val Val Lys Pro Gly Ala Ser
    130                 135                 140
```

```
Val Lys Met Ser Cys Lys Ala Ser Gly Tyr Thr Phe Thr Ser Tyr Asn
145                 150                 155                 160

Met His Trp Val Lys Gln Thr Pro Gly Gln Gly Leu Glu Trp Ile Gly
            165                 170                 175

Tyr Ile Tyr Pro Gly Asn Gly Ala Thr Asn Tyr Asn Gln Lys Phe Gln
            180                 185                 190

Gly Lys Ala Thr Leu Thr Ala Asp Pro Ser Ser Thr Ala Tyr Met
            195                 200                 205

Gln Ile Ser Ser Leu Thr Ser Glu Asp Ser Ala Val Tyr Phe Cys Ala
    210                 215                 220

Arg Gly Asp Ser Val Pro Phe Ala Tyr Trp Gly Gln Gly Thr Leu Val
225                 230                 235                 240

Thr Val Ser Ala Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
            275                 280                 285

Ala Leu Thr Ser Gly Val His Thr Phe Pro Ala Val Leu Gln Ser Ser
            290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
            340                 345                 350

<210> SEQ ID NO 8
<211> LENGTH: 117
<212> TYPE: PRT
<213> ORGANISM: Artificial Sequence
<220> FEATURE:
<223> OTHER INFORMATION: Synthetic peptide

<400> SEQUENCE: 8

Glu Ala Gln Leu Val Gln Ser Gly Ala Glu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Ala Thr Asn Tyr Asn Gln Lys Phe
    50                  55                  60

Gln Gly Lys Ala Thr Leu Thr Ala Asp Pro Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala
        115

<210> SEQ ID NO 9
<211> LENGTH: 108
<212> TYPE: PRT
<213> ORGANISM: Homo sapiens
```

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 10
<211> LENGTH: 1056
<212> TYPE: DNA
<213> ORGANISM: Artificial Sequence
<220> FEATURE:
<223> OTHER INFORMATION: Synthetic oligonucleotide

<400> SEQUENCE: 10

```
gaggcccagc tggtgcagtc tggcgctgag gtggtcaagc ctggggccag cgtgaagatg     60
agctgcaagg ccagcggcta caccttcacc agctacaaca tgcactgggt caagcagacc    120
ccagggcagg gcctggaatg gattggctac atctaccccg caacggcgc caccaactac    180
aaccagaagt tccagggcaa ggctaccctg accgccgacc tagcagcag caccgcctac    240
atgcagatca gcagcctgac cagcgaggac agcgccgtgt acttctgcgc cagaggcgac    300
agcgtgccct cgcctattg gggccagggc accctggtca cagtgtctgc tggtggcgga    360
ggatccggcg gaggcggaag cgaagcccag ctcgtccaga gcggagccga ggtcgtgaaa    420
ccaggcgcct ctgtgaagat gtcttgcaag gcctctggct ataccttac ctcctataat    480
atgcattggg tcaaacagac acctggacag ggactcgagt ggatcggata tatctatcct    540
ggaaatgggg ccacaaatta caatcagaaa tttcagggga agccacact gacagccgat    600
cccagctcct ccacagccta tatgcagatt agctctctga cctccgagga ctccgccgtg    660
tattttgtg cccggggaga ctccgtgcct tttgcttact ggggacaggg cacactcgtg    720
acagtgtccg ccgcttccac caagggcccc tccgtgtttc ctctggcccc cagcagcaag    780
agcacctctg gcggaacagc cgccctgggc tgcctggtca aggactactt ccccgagccc    840
gtgaccgtgt cttggaactc tggcgccctg acctccggcg tccacacctt tccagccgtg    900
ctgcagagca gcggcctgta ctctctgagc agcgtcgtga ccgtgcccag cagcagcctg    960
gggacccaga cctacatctg caacgtgaac cacaagccca gcaacaccaa ggtggacaag   1020
aaggtggaac ccaagagctg cgacaagacc cacacc                             1056
```

<210> SEQ ID NO 11
<211> LENGTH: 1113
<212> TYPE: DNA
<213> ORGANISM: Artificial Sequence
<220> FEATURE:
<223> OTHER INFORMATION: Synthetic oligonucleotide

<400> SEQUENCE: 11

```
atgggctggt cctgcatcat cctgtttctg gtggccacag ccaccggcgt gcactctgag    60
gcccagctgg tgcagtctgg cgctgaggtg gtcaagcctg gggccagcgt gaagatgagc   120
tgcaaggcca gcggctacac cttcaccagc tacaacatgc actgggtcaa gcagacccca   180
ggcagggcc tggaatggat tggctacatc taccccggca acggcgccac caactacaac    240
cagaagttcc agggcaaggc taccctgacc gccgacccta gcagcagcac cgcctacatg   300
cagatcagca gcctgaccag cgaggacagc gccgtgtact ctgcgccag aggcgacagc    360
gtgcccttcg cctattgggg ccagggcacc ctggtcacag tgtctgctgg tggcggagga   420
tccggcggag gcggaagcga agcccagctc gtccagagcg gagccgaggt cgtgaaacca   480
ggcgcctctg tgaagatgtc ttgcaaggcc tctggctata cctttacctc ctataatatg   540
cattgggtca acagacacc tggacaggga ctcgagtgga tcggatatat ctatcctgga    600
aatggggcca caattacaa tcagaaattt caggggaaag ccacactgac agccgatccc    660
agctcctcca cagcctatat gcagattagc tctctgacct ccgaggactc cgccgtgtat   720
ttttgtgccc ggggagactc cgtgccttt gcttactggg gacagggcac actcgtgaca    780
gtgtccgccg cttccaccaa gggccctcc gtgtttcctc tggcccccag cagcaagagc    840
acctctggcg aacagccgc cctgggctgc ctggtcaagg actacttccc cgagcccgtg    900
accgtgtctt ggaactctgg cgccctgacc tccggcgtcc acacctttcc agccgtgctg   960
cagagcagcg gcctgtactc tctgagcagc gtcgtgaccg tgcccagcag cagcctgggg  1020
acccagacct acatctgcaa cgtgaaccac aagcccagca caccaaggt ggacaagaag   1080
gtggaaccca gagctgcga caagacccac acc                                1113
```

<210> SEQ ID NO 12
<211> LENGTH: 231
<212> TYPE: PRT
<213> ORGANISM: Artificial Sequence
<220> FEATURE:
<223> OTHER INFORMATION: Synthetic peptide

<400> SEQUENCE: 12

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Gly Gly Gly Ser Gly Gly
            100                 105                 110

Gly Gly Glu Ala Gln Leu Val Gln Ser Gly Ala Glu Val Val Lys Pro
        115                 120                 125

Gly Ala Ser Val Lys Met Ser Cys Lys Ala Ser Gly Tyr Thr Phe Thr
    130                 135                 140

Ser Tyr Asn Met His Trp Val Lys Gln Thr Pro Gly Gln Gly Leu Glu
145                 150                 155                 160

Trp Ile Gly Tyr Ile Tyr Pro Gly Asn Gly Ala Thr Asn Tyr Asn Gln

```
                      165                 170                 175
Lys Phe Gln Gly Lys Ala Thr Leu Thr Ala Asp Pro Ser Ser Ser Thr
                180                 185                 190

Ala Tyr Met Gln Ile Ser Ser Leu Thr Ser Glu Asp Ser Ala Val Tyr
            195                 200                 205

Phe Cys Ala Arg Gly Asp Ser Val Pro Phe Ala Tyr Trp Gly Gln Gly
        210                 215                 220

Thr Leu Val Thr Val Ser Ala
225                 230

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Gly Gly His His His His His His
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Gly Gly Cys Gly Gly His His His His His His
1               5                   10
```